US012673939B2

(12) United States Patent
Baloglu et al.

(10) Patent No.: US 12,673,939 B2
(45) Date of Patent: Jul. 7, 2026

(54) METHODS OF SYNTHESIS OF HETEROARYL DERIVATIVES OF TRIAZOLYL ACRYLAMIDES AND CRYSTALLINE FORMS

(71) Applicant: Karyopharm Therapeutics Inc., Newton, MA (US)

(72) Inventors: Erkan Baloglu, Stoneham, MA (US); Brian C. Austad, Tewksbury, MA (US); David G. Roe, Rockwood (CA); Andrew Leduc, Wilmington, MA (US); Stephen Edmund Gottschling, N. Aurora (CA); Evan Hecker, Arlington, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 389 days.

(21) Appl. No.: 18/561,374

(22) PCT Filed: May 20, 2022

(86) PCT No.: PCT/US2022/030294

§ 371 (c)(1),
(2) Date: Nov. 16, 2023

(87) PCT Pub. No.: WO2022/246227

PCT Pub. Date: Nov. 24, 2022

(65) Prior Publication Data

US 2024/0287041 A1 Aug. 29, 2024

Related U.S. Application Data

(60) Provisional application No. 63/190,987, filed on May 20, 2021.

(51) Int. Cl.
*C07D 403/06* (2006.01)
*A61K 31/506* (2006.01)

(52) U.S. Cl.
CPC .......... *C07D 403/06* (2013.01); *A61K 31/506* (2013.01)

(58) Field of Classification Search
None
See application file for complete search history.

(56) References Cited

U.S. PATENT DOCUMENTS 9,738,624 B2 8/2017 Baloglu et al.
10,407,405 B2 9/2019 Baloglu et al.
(Continued)

FOREIGN PATENT DOCUMENTS

WO WO-2014/205389 A1 12/2014
WO WO-2017/117529 A1 7/2017
WO WO-2022/246227 A1 11/2022

OTHER PUBLICATIONS

International Search Report and Written Opinion for International Application No. PCT/US2022/030294 dated Oct. 21, 2022.
(Continued)

*Primary Examiner* — Samantha L Shterengarts
(74) *Attorney, Agent, or Firm* — FOLEY HOAG LLP

(57) ABSTRACT

The present invention relates to a method of preparing a compound represented by structural formula (VII), comprising reacting a compound represented by structural formula (II), with a compound represented by structural formula (III), in a solvent, in the presence of a Pd catalyst and one or more inorganic bases under conditions suitable to prepare a compound represented by structural formula (VII): The values and example values of the variables in structural formulas (VII), (II), and (III) are defined herein. The present invention also relates to crystalline Forms I and II of the compound represented by Structural Formula (VII), the use of the crystalline Forms in treating disease or disorders associated with CRM1 and method of preparing the crystalline Forms.

(VII)

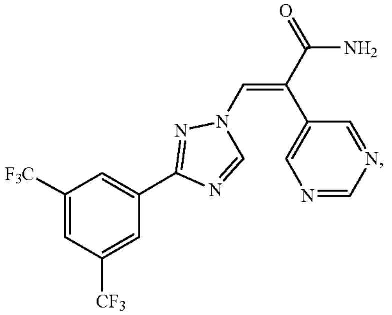

(II)

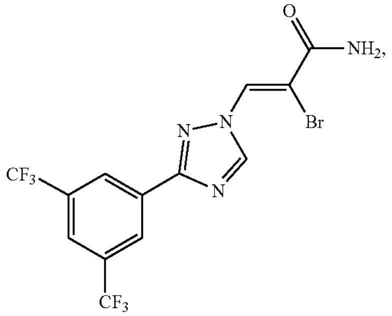

(III)

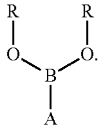

21 Claims, 27 Drawing Sheets

(56) References Cited

U.S. PATENT DOCUMENTS

| | | | |
|---|---|---|---|
| 10,519,139 | B2 | 12/2019 | Austad et al. |
| 11,078,190 | B2 | 8/2021 | Austad et al. |
| 11,124,493 | B2 | 9/2021 | Baloglu et al. |
| 11,746,102 | B2 | 9/2023 | Austad et al. |
| 11,753,401 | B2 | 9/2023 | Austad et al. |
| 11,807,629 | B2 | 11/2023 | Austad et al. |
| 11,945,794 | B2 | 4/2024 | Baloglu et al. |

OTHER PUBLICATIONS

Invitation to Pay Additional Fees for International Application No. PCT/US2022/030294 dated Aug. 12, 2022.

| | | | | 4 h IPC (%a/a) | | | | | | | | | 24 h IPC (%a/a) | | | | | | | | |
|---|---|---|---|---|---|---|---|---|---|---|---|---|---|---|---|---|---|---|---|---|---|
| | | | TC | MC0 | MB6 | MB3/ MC8 | MB9 | MB5 | PF9 | | | | MC0 | MB6 | MB3/ MC8 | MB9 | MB5 | PF9 | | | |
| | | | KPT# | 8781 | 8602 | 9508 | | 7538 | | | | | 8781 | 8602 | 9508 | | 7538 | | | | |
| | | | m/z | 429 | 429 | 351 | 429/ 431 | 429/431 | 699 | | 630 | | 429 | 429 | 351 | 429/ 431 | 429/431 | 699 | | 630 | |
| Entry | Exp (1457-PK-) | Catalyst | RT | 2.9 | 3.0 | 3.2 | 3.3 | 3.5 | 3.9 | 4.1 | 4.2 | Conversion | 2.9 | 3.0 | 3.2 | 3.3 | 3.5 | 3.9 | 4.1 | 4.2 | Conversion |
| 1 | 134-R1 | $PdDPPFCl_2DCM$ *(control)* | | 5.2 | 34.2 | 15.8 | 2.3 | 28.9 | 2.3 | 0.0 | 0.0 | 71.1 | 5.4 | 38.6 | 18.1 | 2.3 | 28.3 | 3.7 | 0.0 | 0.0 | 71.7 |
| 2 | 134-R2 | QPhosPd(Crotyl)Cl | | 0.0 | 7.1 | 6.0 | 2.2 | 77.0 | 2.4 | 0.0 | 0.0 | 23.0 | 0.0 | 11.0 | 16.0 | 7.5 | 54.0 | 0.0 | 2.6 | 7.6 | 46.0 |
| 3 | 134-R3 | AmPhos Pd(crotyl)Cl | | 0.0 | 73.6 | 1.5 | 0.0 | 22.0 | 2.9 | 0.0 | 0.0 | 78.0 | 0.0 | 68.9 | 1.8 | 0.0 | 18.7 | 3.6 | 6.8 | 0.0 | 81.3 |
| 4 | 134-R4 | [P(tBu)3] Pd(crotyl)Cl | | 0.3 | 83.0 | 2.9 | 0.0 | 7.9 | 2.3 | 0.0 | 0.0 | 92.1 | 0.0 | 84.1 | 3.8 | 0.0 | 6.5 | 2.6 | 0.0 | 0.0 | 93.5 |
| 5 | 134-R5 | XPhos Pd(crotyl)Cl | | 2.7 | 17.0 | 5.8 | 0.0 | 61.9 | 6.2 | 0.0 | 0.0 | 38.1 | 3.3 | 22.7 | 10.6 | 0.0 | 56.7 | 6.7 | 0.0 | 0.0 | 43.3 |
| 6 | 134-R6 | RuPhos Pd(crotyl)Cl | | 0.0 | 12.9 | 15.9 | 10.7 | 47.6 | 0.0 | 0.0 | 2.0 | 52.4 | 1.8 | 15.1 | 22.3 | 12.7 | 28.2 | 1.0 | 1.7 | 7.0 | 71.8 |
| 7 | 134-R7 | SPhos Pd(crotyl)Cl | | 2.5 | 29.5 | 12.0 | 3.9 | 43.9 | 1.1 | 0.0 | 0.0 | 56.1 | 3.6 | 47.8 | 18.4 | 3.5 | 19.6 | 2.3 | 0.0 | 0.0 | 80.4 |
| 8 | 134-R8 | [BrettPhos Pd(crotyl)]OTf | | 0.6 | 4.2 | 6.1 | 2.5 | 86.0 | 0.0 | 0.0 | 0.0 | 14.0 | 0.0 | 7.0 | 13.9 | 5.7 | 62.9 | 0.0 | 0.0 | 9.0 | 37.1 |
| 9 | 134-R9 | [(R)-BINAP Pd(allyl)]Cl | | 0.0 | 0.0 | 3.6 | 3.4 | 83.8 | 8.2 | 0.0 | 0.0 | 16.2 | 0.0 | 0.0 | 7.8 | 7.9 | 67.5 | 9.0 | 0.0 | 4.0 | 32.5 |
| 10 | 134-R10 | [XantPhos Pd(allyl)]Cl | | 0.3 | 4.0 | 3.4 | 3.1 | 83.5 | 0.0 | 0.0 | 0.0 | 16.5 | 0.0 | 9.0 | 12.2 | 6.4 | 58.1 | 0.0 | 0.0 | 9.4 | 41.9 |
| 11 | 136-R1 | [P(tBu)3] Pd(crotyl)Cl | | 0.0 | 87.0 | 4.8 | 0.0 | 4.7 | 3.3 | 0.0 | 0.0 | 95.3 | 0.0 | 87.0 | 5.7 | 0.0 | 2.8 | 3.1 | 0.0 | 0.0 | 97.2 |
| 12 | 136-R2 | [P(Cy)3] Pd(crotyl)Cl | | 0.0 | 41.0 | 6.5 | 0.0 | 46.0 | 2.1 | 0.0 | 0.0 | 54.0 | 0.7 | 67.9 | 11.2 | 0.0 | 5.0 | 5.3 | 0.0 | 0.0 | 95.0 |

FIG. 2

| | | | | | 4 h IPC (%a/a) | | | | | | | | |
|---|---|---|---|---|---|---|---|---|---|---|---|---|---|
| | | | | TC | MC0 | MB6 | MB3/ MC8 | MB9 | MB5 | PF9 | | | |
| | | | | KPT# | 8781 | 8602 | 9508 | | 7538 | | | | |
| | | | | m/z | 429 | 429 | 351 | 429/ 431 | 429/431 | 699 | | 630 | |
| Entry | Exp (1457-PK-) | Org A (pts.) | Solvent B (pts.) | RT | 2.9 | 3.0 | 3.2 | 3.3 | 3.5 | 3.9 | 4.1 | 4.2 | Conversion |
| 1 | 138-R1 | Dioxane (30) | $H_2O$ (6) | | 5.2 | 83.0 | 9.6 | 0.0 | 0.0 | 1.9 | 0.0 | 0.0 | 100.0 |
| 2 | 138-R2 | THF (30) | $H_2O$ (6) | | 0.0 | 85.0 | 9.9 | 0.0 | 0.0 | 3.6 | 0.0 | 0.0 | 100.0 |
| 3 | 138-R3 | MeTHF (30) | $H_2O$ (6) | | 0.0 | 72.0 | 8.7 | 0.0 | 0.0 | 6.3 | 0.0 | 0.0 | 90.3 |
| 4 | 138-R4 | EtOH/MeTHF (45) | $H_2O$ (6) | | 1.6 | 75.0 | 17.0 | 0.0 | 0.0 | 1.8 | 0.0 | 0.0 | 100.0 |
| 5 | 138-R5 | Tol/MeTHF (45) | $H_2O$ (6) | | 0.0 | 31.8 | 11.4 | 0.0 | 51.5 | 1.5 | 0.0 | 0.0 | 48.5 |

Notes:

1. All experiments were carried out using 3 mol% catalyst [P(tBu)$_3$] Pd(crotyl)Cl loading and 0.5 eq. of $Cs_2CO_3$ at 70 °C (except THF – reflux).
2. Data was only collected at the 4 hour time point.
3. The impurity with m/z = 351 was initially identified as MB3 based on mass, but was likely MC8 based on retention time and expected stereochemistry of the debromination side reaction. MC8 was identified as the major debromination product by authentic spiking in later experiments.

FIG. 3

| | | | | | | 24 h IPC (%a/a) | | | | | | | | | 24 h IPC (%a/a) | | | | | | | | |
|---|---|---|---|---|---|---|---|---|---|---|---|---|---|---|---|---|---|---|---|---|---|---|---|
| | | | | | TC | MC 0 | MB 6 | MB3 / MC8 | MB 9 | MB5 | PF 9 | | | | MC 0 | MB 6 | MB3 / MC8 | MB 9 | MB5 | PF 9 | | | |
| | | | | | KPT # | 8781 | 8602 | 9508 | | 7538 | | | | | 8781 | 8602 | 9508 | | 7538 | | | | |
| | | | | | m/z | 429 | 429 | 351 | 429/431 | 429/431 | 699 | | 630 | | 429 | 429 | 351 | 429/431 | 429/431 | 699 | | 630 | |
| Entry | Exp (1457-PK-) | Catalyst | Org A (pts.) | Base (eq.) | RT | 2.9 | 3.0 | 3.2 | 3.3 | 3.5 | 3.9 | 4.1 | 4.2 | Conversion | 2.9 | 3.0 | 3.2 | 3.3 | 3.5 | 3.9 | 4.1 | 4.2 | Conversion |
| 1 | 140-R1 | AmPhos Pd(crotyl)Cl | Dioxane (30) | $Cs_2CO_3$ (0.5) | | 0.0 | 70.5 | 6.6 | 0.0 | 19.5 | 3.3 | 0 | 0.0 | 80.5 | ND | ND | ND | ND | ND | ND | ND | ND | ND |
| 2 | 140-R2 | AmPhos Pd(crotyl)Cl | Dioxane (30) | $Cs_2CO_3$ (1) | | 0.9 | 47.9 | 15.9 | 3.0 | 30.1 | 1.5 | 0 | 0.0 | 69.9 | ND | ND | ND | ND | ND | ND | ND | ND | ND |
| 3 | 144-R1 | [P(tBu)3] Pd(crotyl)Cl | MeTHF (30) | $Cs_2CO_3$ (1) | | 1.0 | 63.9 | 15.0 | 3.0 | 15.9 | 0.0 | 0.0 | 0.0 | 84.1 | 1.4 | 69.0 | 19.8 | 3.3 | 3.1 | 2.3 | 0.0 | 0.0 | 96.9 |
| 4 | 144-R2 | [P(tBu)3] Pd(crotyl)Cl | MeTHF (30) | $NaHCO_3$ (2) | | 0.8 | 46.9 | 12.4 | 3.1 | 35.5 | 0.0 | 0.0 | 0.0 | 64.5 | 1.5 | 51.6 | 16.2 | 3.6 | 20.1 | 1.9 | 0.0 | 0.0 | 79.9 |
| 5 | 144-R3 | [P(tBu)3] Pd(crotyl)Cl | MeTHF (30) | $K_2CO_3$ (1) | | 0.7 | 55.6 | 12.1 | 2.8 | 25.2 | 0.0 | 0.0 | 1.9 | 74.8 | 1.1 | 68.8 | 17.9 | 3.3 | 5.8 | 2.2 | 0.0 | 0.0 | 94.2 |
| 6 | 144-R4 | [P(tBu)3] Pd(crotyl)Cl | MeTHF (30) | $K_3PO_4$ (2) | | 0.7 | 55.6 | 12.1 | 2.8 | 25.3 | 0.0 | 0.0 | 1.8 | 74.7 | 7.1 | 55.7 | 21.8 | 3.4 | 12.5 | 1.6 | 0.0 | 0.0 | 87.5 |

Notes:

1. All experiments were carried out using 3 mol% catalyst loading in 30 pts of solvent A (dioxane or MeTHF) and 6 pts of solvent B (water) at 70 °C.
2. ND = not determined.
3. The impurity with m/z = 351 was initially identified as MB3 based on mass, (LCMS), but was likely MC8 based on retention time and expected stereochemistry of the debromination side reaction. MC8 was identified as the major debromination product by authentic spiking in later experiments.

FIG. 4

| No | Reaction Conditions (MB5: 1.0 eq; MB7: 2.0 eq; $Cs_2CO_3$: 0.5 eq; 5g) | Pd Catalyst | IPC Result (MB5 wrt MB6 % a/a) | MB6 Purity in Reaction Mixture (% a/a) | Major By-products wrt MB6 (% a/a) | Conclusions | Ref. |
|---|---|---|---|---|---|---|---|
| 1 | Degassed THF:$H_2O$ 7:1 (16 parts); at reflux (65 °C); 4 hrs | $^tBu_3PPd(crotyl)Cl$, 3% | 115 | 37 | MC8: 21.3<br>PF9: 1.5 | 1.Reaction stalled<br>2.High levels of by-products | 1473-JZ-001 |
| 2 | Degassed THF:$H_2O$ 15:2 (34 parts); at reflux (63 °C); 6 hrs | $^tBu_3PPd(crotyl)Cl$, 3% | 1.1 | 80 | MC8: 7.9<br>PF9: 3.7 | High levels of by-products | 1473-JZ-004 |
| 3 | Degassed THF:$H_2O$ 15:2 (34 parts); at reflux (63 °C); 8 hrs | $^tBu_3PPd(crotyl)Cl$, 3% | 86 | 43 | MC8: 22<br>PF9: 3.2 | High levels of by-products | 1473-JZ-009 |
| 4 | Repeated the above trial using a new lot Pd catalyst | $^tBu_3PPd(crotyl)Cl$, 3% | Almost no reaction | - | - | No reaction | 1473-JZ-018 |
| 5 | Degassed dioxane:$H_2O$ 15:2 (34 parts); 70-76 °C; 4 hrs | $^tBu_3PPd(crotyl)Cl$, 3% | 86 | 37 | MC8: 29<br>PF9: 9.0 | 1.Reaction stalled<br>2.High levels of by-products | 1473-JZ-007 |

FIG. 5

| No | Reaction Conditions (MB5: 1.0 eq; MB7: 2.0 eq; $Cs_2CO_3$: 0.5 eq) | Pd Catalyst | IPC Result (MB5 wrt MB6 % a/a) | MB6 Purity in Reaction Mixture (% a/a) | Major By-products wrt MB6 (% a/a) | Conclusions | Ref. |
|---|---|---|---|---|---|---|---|
| 1 | Degassed THF:$H_2O$ 15:2 (17 parts); at reflux (64 °C); 7 hrs | Strem Pd 46-0232, 2% | Almost no reaction | - | - | No reaction | 1473-JZ-013 |
| 2 | Degassed THF:$H_2O$ 15:2 (17 parts); at reflux (64 °C); 7 hrs | Strem SPhos Palladacycle Gen. 2 (Cat #46-0283), 2% | Almost no reaction | - | - | No reaction | 1473-JZ-015 |
| 3 | Degassed THF:$H_2O$ 15:2 (17 parts); at reflux (63 °C); 8 hrs | Strem Amphos Palladacycle Gen. 2 (Cat #46-0342), 2% | 10.9 | 76.1 | MC8: 3.1<br>PF9: 13.7 | 1.Reaction stalled<br>2.High levels of by-products | 1473-JZ-011 |
| 4 | Degassed THF:$H_2O$ 15:2 (22 parts); at reflux (63 °C); 7 hrs | Strem Amphos Palladacycle Gen. 2 (Cat #46-0342), 3% | 4.8 | 77.6 | MC8: 13.9<br>PF9: 9.7 | 1.Reaction stalled<br>2.High levels of by-products | 1473-JZ-016 |
| 5 | Degassed dioxane:$H_2O$ 15:2 (34 parts); 70-76 °C; 4 hrs | Strem Amphos Palladacycle Gen. 2 (Cat #46-0342), 3% | No MB5 detected | 89.2 | MC8: 1.6<br>PF9: 3.1 | Good reaction | 1473-JZ-019 |
| 6 | Repeated the above trial at 11g scale | Strem Amphos Palladacycle Gen. 2 (Cat #46-0342), 3% | 0.1 | 86.5 | MC8: 0.6<br>PF9: 3.0 | Good reaction | 1473-JZ-028 |
| 7 | Degassed dioxane:$H_2O$ 15:2 (34 parts); 60-65 °C; 4 hrs | JM Amphos Pd(crotyl)Cl (Pd-161), 3% | No MB5 detected | 88.3 | MC8: 1.7<br>PF9: 3.8 | Good reaction | 1473-JZ-021 |

FIG. 6

| No | Reaction Conditions (MB7: 2.0 eq; $Cs_2CO_3$; 0.5 eq; 5g scale) | Amount of Strem Amphos Paladacycle Gen. 2 | IPC Result (% a/aMB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | Degassed dioxane:$H_2O$ (7:1, 24 parts); 60-65 °C; 4 hrs | 3 mol % | 0.1 | 87.7 | 0.5 | 2.2 | 2.6 | Good result | 1473-JZ-153 |
| 2 | Degassed dioxane:$H_2O$ (7:1, 24 parts); 60-65 °C; 4 hrs | 2 mol % | 0.2 | 85.5 | 0.3 | 2.6 | 3.9 | Good result | 1473-JZ-155 |
| 3 | Degassed dioxane:$H_2O$ (7:1, 24 parts); 60-65 °C; 4 hrs | 1 mol % | 19.0 | 70.1 | 0.3 | 4.5 | 2.0 | Reaction stalled | 1473-JZ-157 |

FIG. 7

| No | Reaction Conditions (MB7: 2.0 eq; $Cs_2CO_3$; 0.5 eq; 5g scale) | Amount of MB7 (Eq) | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | 3% Strem Pd 46-0342, 24 parts of degassed dioxane: $H_20$ 7:1, 60-65 °C, 4 hrs | 1.5 | 9.0<br>8.4 after 7 hours | 80.8 | 0.2 | 2.0 | 5.1 | Reaction stalled even extending the reaction time | 1473-JZ-141 |
| 2 | 3% Strem Pd 46-0342, 34 parts of degassed dioxane: $H_20$ 7:1, 60-65 °C, 4 hrs | 1.5 | 9.6<br>8.8 after 9 hours | 81.3 | 0.2 | 1.9 | 4.6 | Reaction stalled even extending the reaction time | 1473-JZ-151 |
| 3 | 2% Strem Pd 46-0342, 24 parts of degassed | 1.8 | 0.6 | 88.2 | 0.1 | 1.7 | 2.9 | Good result, but the residual MB5 | 1499-JZ-001 |

FIG. 8

| No | Reaction Conditions (2.0 eq MB7: 0.5 eq $Cs_2CO_3$; 2% Strem Pd 46-0342; 5g scale) | Degassed Solvents | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | 3% Strem Pd 46-0342; 60-65 °C; 4 hrs | Degassed dioxane:$H_2O$ 7:1 24 parts | 0.1 | 87.7 | 0.5 | 2.2 | 2.6 | Good result | 1473-JZ-153 |
| 2 | 60-65 °C; 4 hrs | Degassed THF:$H_2O$ 3:1 24 parts | 3.6 | 75.6 | 0.2 | 11.0 | 2.9 | Reaction stalled and higher level Impurities | 1473-JZ-161 |
| 3 | 60-65 °C; 4 hrs | Degassed THF:$H_2O$ 1:1 24 parts | 0.03 | 79.5 | 1.6 | 9.2 | 2.0 | Higher level Impurities | 1473-JZ-163 |
| 4 | 60-65 °C; 4 hrs | Degassed MeOH:$H_2O$ 5:1 24 parts | 0.6 | 58.5 | 4.6 | 32.1 | 3.0 | Higher level Impurities | 1473-JZ-162 |
| 5 | 60-65 °C; 4 hrs<br><br>8 hours more | Degassed MeTHF:$H_2O$ 7:1, 24 parts | 36.8<br><br>14.8 | 66.4<br><br>72.5 | 0.1<br><br>0.1 | 2.1<br><br>2.7 | 5.5<br><br>10.8 | Reaction stalled<br><br>Reaction stalled again and higher level PF9 | 1473-JZ-169 |

FIG. 9

| No | Reaction Conditions (MB7: 2.0 eq; $Cs_2CO_3$; 0.5 eq; 2% Strem Pd 46-0342); 5g scale | Degassed Dioxane:$H_2O$ Ratio (v/v) | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | 24 parts solvents; 60-65 °C; 8 hrs | 14:1 | 6.6<br><br>3.9 after 13 hours | 83.5<br><br>84.2 after 13 hours | 0.2<br><br>0.2 | 1.9<br><br>2.0 | 3.4<br><br>4.4 | Reaction stalled even extending the reaction time | 1473-JZ-174 |
| 2 | 24 parts solvents; 60-65 °C; 4 hrs | 7:1 | 0.2 | 85.5 | 0.3 | 2.6 | 3.9 | Good reaction | 1473-JZ-155 |
| 3 | 24 parts solvents; 60-65 °C; 4 hrs | 2:1 | 0.1 | 80.9 | 3.5 | 6.4 | 0.9 | Higher level Impurities than the above one | 1473-JZ-165 |

FIG. 10

| No | Reaction Conditions (2.0 eq MB7; 0.5 eq $Cs_2CO_3$; 5g scale) | Degassed Dioxane:$H_2O$ 7:1 v/v Parts | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | 3% Strem Pd 46-0342; 60-65 °C; 4 hrs | 34 | No MB5 detected | 89.2 | 0.7 | 1.6 | 3.1 | Good reaction | 1473-JZ-019 |
| 2 | 3% Strem Pd 46-0342; 60-65 °C; 4 hrs | 24 | 0.1 | 87.2 | 0.5 | 2.2 | 3.4 | Good reaction | 1473-JZ-153 |
| 3 | 2% Strem Pd 46-0342; 60-65 °C; 4 hrs | 24 | 0.2 | 85.5 | 0.3 | 2.6 | 3.9 | Good reaction too, comparing with above one | 1473-JZ-155 |
| 4 | 2% Strem Pd 46-0342; 55-60 °C; 5.5 hrs | 24 | 0.1 | 87.9 | 0.3 | 2.1 | 3.9 | Good reaction too, comparing with above one | 1473-JZ-180 |
| 5 | 2% Strem Pd 46-0342; 60-65 °C; 6 hrs | 18 | 0.9 | 86.3 | 0.1 | 2.4 | 4.8 | Good reaction, but the residual MB5 close to the limit (<1%) | 1473-JZ-172 |
| 6 | Reducing top volume to 12 parts, | 12 | 9.6 | 79.0 | 0.1 | 2.7 | 3.5 | Reaction stalled. A biphasic mixture | 1473-JZ-167 |

FIG. 11

| No | Reaction Conditions (MB7: 2.0 eq; $Cs_2CO_3$: 0.5 eq; 24 parts of degassed dioxane:$H_2O$ 7:1; 2% Strem Pd 46-0342); 5g scale | Reaction Time Needed | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | 50-55 °C | 14 hrs | 1.3 | 86.8 | 0.1 | 2.1 | 3.1 | Cleaner reaction, but required longer time | 1473-JZ-177 |
| 2 | 55-60 °C | 5.5 hrs | 0.1 | 87.9 | 0.3 | 2.1 | 3.9 | Best one | 1473-JZ-180 |
| 3 | 60-65 °C | 4 hrs | 0.2 | 85.5 | 0.3 | 2.6 | 3.9 | Good one | 1473-JZ-155 |
| 4 | Reflux (71-72 °C) | 4 hrs | 0.1 | 79.4 | 5.8 | 3.0 | 4.8 | Much higher level of MC0 | 1473-JZ-176 |

FIG. 12

| No | Reaction Conditions | Time for Reaction Mixture Degassing After Reagents Combined | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | MB7: 2.0 eq; $Cs_2CO_3$: 0.5 eq; 24 parts of degassed dioxane:$H_2O$ 7:1; 2% Strem Pd 46-0342; 55-60 °C; 8.5 hrs; 5g scale | 55 min. | N/D | 85.9 | 0.1 | 2.4 | 3.9 | Good reaction | 1473-JZ-180 |
| 2 | MB7: 2.0 eq; $Cs_2CO_3$: 0.5 eq; 24 parts of degassed dioxane:$H_2O$ 7:1; 2% Strem Pd 46-0342; 55-60 °C; 7 hrs; 5g scale | 0 min. | 0.08 | 89.2 | 0.1 | 2.0 | 2.9 | Comparable one, even though no degassing of the reaction mixture before heating | 1473-JZ-203 |

FIG. 13

| No | Reaction Conditions (2.0 eq MB7; 2% Strem Pd 46-0342; 5g scale) | Base | IPC Result (% a/a MB5 wrt MB6) | MB6 Purity in Reaction Mixture (% a/a) | MC0 wrt MB6 (% a/a) | MC8 wrt MB6 (% a/a) | PF9 wrt MB6 (% a/a) | Note | Ref. |
|---|---|---|---|---|---|---|---|---|---|
| 1 | Degassed dioxane:$H_2O$ (7:1, 24 parts); 60-65 °C; 4 hrs | $Cs_2CO_3$ 0.5 eq | 0.1 | 87.7 | 0.5 | 2.2 | 2.6 | Good reaction | 1473-JZ-180 |
| 2 | Degassed dioxane:$H_2O$ (7:1, 24 parts); 60-65 °C; 4 hrs | $K_3PO_4$ 0.5 eq | 29.4 | 67.0 | 0.1 | 2.9 | 5.2 | Reaction stalled | 1473-JZ-159 |
| 3 | Degassed dioxane:$H_2O$ (7:1, 24 parts); 60-65 °C; 7.5 hrs | $Cs_2CO_3$/$CsHCO_3$ 0.25 eq each | 34.0 | 65.3 | 0.1 | 2.9 | 3.7 | Reaction stalled | 1499-JZ-026 |
| | Charged more $CsHCO_3$ and heated for 5 more hrs | 0.25 eq more $CsCO_3$ | N/D after 5 hrs | 84.5 after 5 hrs | 0.1 | 2.7 | 5.7 | Good reaction after charging more base | |
| 4 | Degassed dioxane:$H_2O$ (7:1, 24 parts); 55-60 °C; 7.5 hrs | $Cs_2CO_3$/CsOH 0.25 eq/0.50 eq | N/D | 86.8 | 0.1 | 2.4 | 3.8 | As good as $Cs_2CO_3$. Similar impurity profile | 1499-JZ-034 |

FIG. 14

| Entry | Parameter | Change | Comment |
|---|---|---|---|
| 1 | Catalyst Type | Catalyst changed from tetrakis(triphenylphosphine)palladium to Strem Amphos Palladacycle Gen. 2, cat. #46-0342 | High conversion, less side reactions |
| 2 | Catalyst loading | Loading Reduced from 10 mol% to 2 mol% | Potential reduce in cost and lower burden on Pd removal |
| 3 | MB7 eq. | Increased form 1.5 eq. to 2.0 eq. | Increased cost and burden on isolation purging<br><br>Offset by significant increase in performance and yield. Purging studies indicate that MB7 can be effectively purged |
| 4 | $Cs_2Co_3$ eq. | Decreased from 0.75 eq. to 0.50 eq. | Reduced cost and lower side reactions |
| 5 | Dioxane volume | Increased from 16 pts to 21 pts. | Ensures single phase reaction to improve robustness |
| 6 | Water Volume | Increased from 2 pts to 3 pts | Ensures single phase |

FIG. 15A

| Entry | Parameter | Change | Comment |
|---|---|---|---|
| | | | reaction to improve robustness |
| 7 | Reaction Temperature | Reduced from 70-75°C to 55-60 °C | Less energy intensive and lower side reactions |
| 8 | Reaction Time | Reduced from 24 hours to ~7 hours | Reduced cycle times. |

FIG. 15B

Run Time 32.0 Minutes Wavelength: PDA 260.0 nm

Full Scale

| | Name | RT | Area | % Area | In: Type | USP Plate Count | USP Talling | USP Resolution |
|---|---|---|---|---|---|---|---|---|
| 1 | | 2.294 | 168.44 | 0.00 | bb | 3224 | 0.867 | |
| 2 | | 4.752 | 1488.90 | 0.01 | bb | 11843 | 0.812 | 16.677 |
| 3 | | 10.032 | 534.76 | 0.00 | bb | 38200 | 0.821 | 21.444 |
| 4 | | 10.821 | 459.18 | 0.00 | bb | 34997 | 0.661 | 2.742 |
| 5 | MB3 | 12.609 | 13898415.37 | 98.27 | bv | 23056 | 0.794 | 5.719 |
| 6 | MC8 | 14.668 | 62154.46 | 0.44 | vb | 36375 | 0.906 | 6.595 |
| 7 | KG1 | 15.680 | 140789.13 | 1.00 | bb | 50950 | 0.971 | 3.521 |
| 8 | KG5 | 17.774 | 38882.03 | 0.27 | bb | 70027 | 0.937 | 7.719 |
| Sum | | | 14142892.3 | | | | | |

METHODS OF SYNTHESIS OF HETEROARYL DERIVATIVES OF TRIAZOLYL ACRYLAMIDES AND CRYSTALLINE FORMS

This application is the U.S. National Stage of International Application No. PCT/US2022/30294, filed May 20, 2022, which designates the U.S., published in English, and claims the benefit of U.S. Provisional Application No. 63/190,987, filed on May 20, 2021. The entire teachings of the above applications are incorporated herein by reference.

BACKGROUND OF THE INVENTION

Certain triazolyl acrylamides, notably phenyltriazolyl acrylamides, are useful as selective inhibitors of nuclear export (SINEs) and, in particular, as anti-cancer medication. Such phenyltriazolyl acrylamides work by binding to exportin 1 (XPO1 or CRM1), thus blocking the transport of several proteins involved in cancer-cell growth from the cell nucleus to the cytoplasm, which ultimately arrests the cell cycle and leads to apoptosis. Synthetic methods employed for manufacturing these SINEs are multistep schemes requiring tight control of conditions to ensure acceptable yield and stereoselectivity. There is a need for robust, high-yield synthetic methods to produce such SINEs on industrial scale.

In addition to the need for high yield synthetic methods there is also a need for crystalline forms of SINE compounds as such forms can be important in the formulation of pharmaceutical compositions.

SUMMARY OF THE INVENTION

The present invention relates to crystalline Forms I and II of the compound represented by Structural Formula (VII), compositions comprising crystalline Forms I and II, methods of treatment comprising administering crystalline Form I or crystalline Form II or compositions comprising crystalline Forms I or crystalline Form II for the treatment of CRM-1 associated diseases or disorders and methods of making the compound represented by Structural Formula (VII) and crystalline forms of the compound (e.g., crystalline Forms I and II).

In an example embodiment, the present invention is a method of preparing a compound represented by structural formula (VII), (VII)

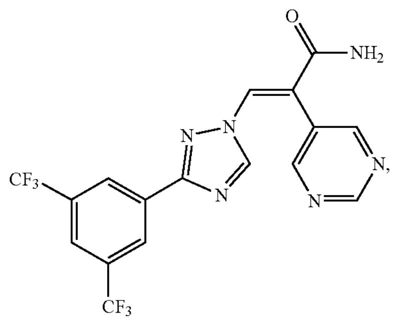

The method comprises: reacting a compound represented by structural formula (II)

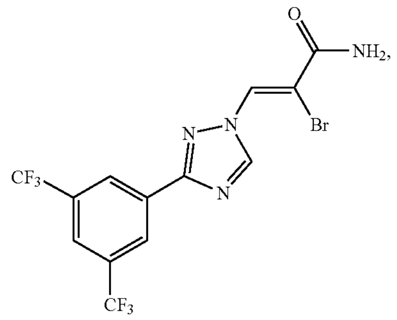

with a compound represented by structural formula (III), (III)

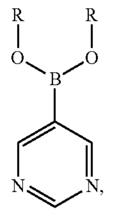

in a first solvent, in the presence of a Pd catalyst and one or more inorganic bases under conditions suitable to prepare a compound represented by structural formula (VII), wherein: each R is hydrogen, a $C_1$-$C_4$ alkyl, or two groups R, taken together with the oxygen atoms to which they are attached, form a 5-7 member cyclic acetal moiety, and thereby obtaining the compound represented by structural formula (VII).

In another example embodiment, the present invention is a compound represented by structural formula (V)

(V)

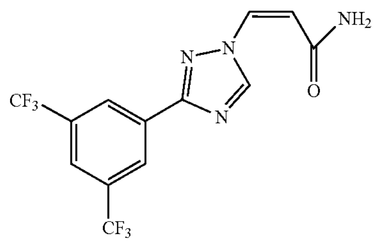

or a salt thereof.

In another example embodiment, the present invention is crystalline Form I of the compound represented by structural formula (VII):

(VII)

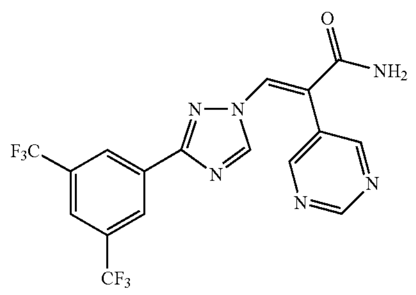

wherein the crystalline form is Form I characterized by X-ray powder diffraction peaks at 2θ angles 4.6°, 22.8°, 23.2°, and 24.4°.

In yet another example embodiment, the present invention is crystalline Form II of the compound represented by structural formula (VII):

(VII)

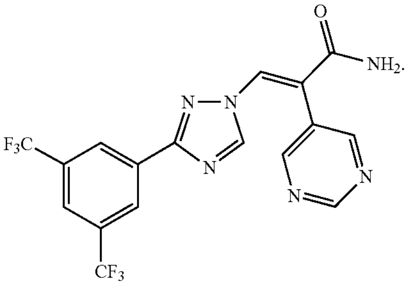

wherein the crystalline form is Form II is characterized by X-ray powder diffraction peaks at 2θ angles 9.9°, 19.2°, 22.4°, and 24.4°.

In another embodiment, the present invention relates to a pharmaceutical composition comprising a crystalline form of the compound represented by Structural Formula (VII) (e.g., crystalline Form I or crystalline Form II) and a pharmaceutically acceptable carrier.

In another embodiment, the present invention relates to a method for treating or preventing a CRM1-associated disease or disorder, the method comprising administering to a subject in need thereof a therapeutically or prophylactically effective amount of the crystalline form (e.g, crystalline Form I or crystalline Form II) of the compound represented by Structural Formula (VII) as described herein.

In another embodiment, the present invention relates to the use of crystalline Form I or crystalline Form II as described herein for treating a CRM-1 associated disease or disorder as described herein in a subject in need thereof.

In yet another embodiment, the present invention relates the use of crystalline Form 1 or crystalline Form II as described herein for the manufacture of a medicament for treating a CRM-1 associated disease or disorder as described herein in a subject in need thereof.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2 depicts a table summarizing the results of the initial Pd catalyst assessment.

FIG. 3 depicts a table summarizing the results of screening of the reaction solvents for the Pd catalytic reaction.

FIG. 4 is a table summarizing the results of screening inorganic bases.

FIG. 5 is table summarizing the results of screening for the reaction conditions of the catalytic reaction.

FIG. 6 is a table summarizing the results of screening catalysts

FIG. 7 is a table summarizing the results of experiments that were carried out to examine the effect of catalyst stoichiometry on the performance of the chemistry.

FIG. 8 is a table summarizing the results of experiments carried out to explore the lower boundary for MB7 equivalents.

FIG. 9 is a table summarizing the results of solvent screening for the Suzuki coupling.

FIG. 10 is a table summarizing the results of experiments testing the ratios of dioxane:water solvent system.

FIG. 11 is a table summarizing the results of testing the effect of total solvent volume on Suzuki coupling reaction.

FIG. 12 is a table summarizing the results of evaluating reaction temperature for the Suzuki coupling.

FIG. 13 is a table comparing the results of the degassed and non-degassed reactions for the Suzuki coupling.

FIG. 14 is a table summarizing experiments evaluating the effect of pH on the Suzuki coupling reaction.

FIG. 15A and FIG. 15B, collectively, present a summary of notable changes and improvements of the synthetic methods disclosed herein relative to the prior procedures.

DETAILED DESCRIPTION OF THE INVENTION

Figure 1:
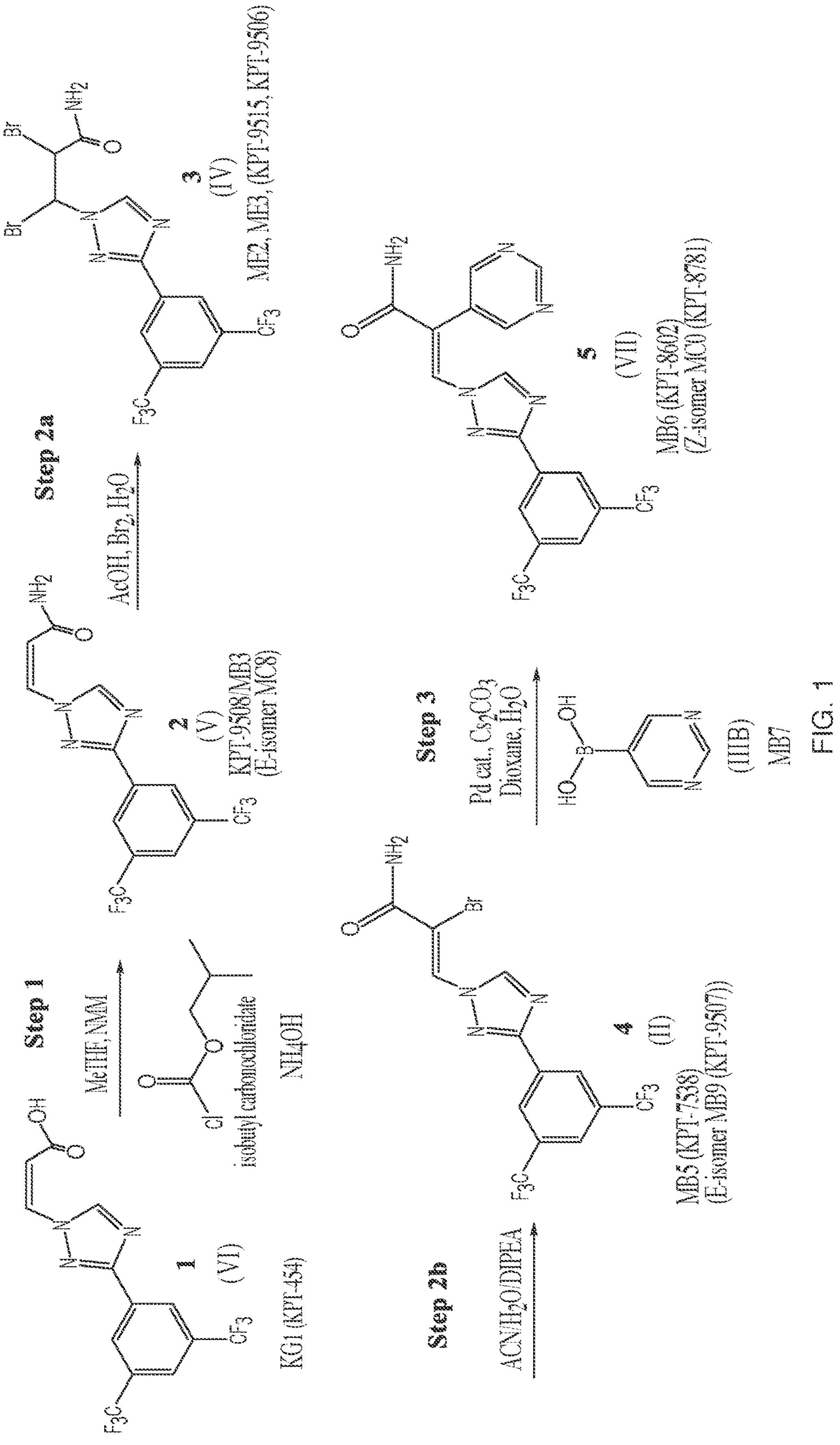
FIG. 1 depicts the overall synthetic scheme according to one aspect of an example embodiment.

A description of example embodiments of the invention follows.

Process:

In a first example embodiment, the present invention is a method of preparing a compound represented by structural formula (VII), (VII)

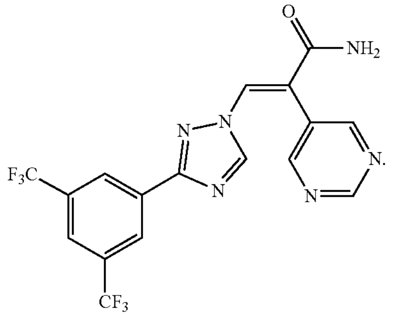

In a first aspect of the first example embodiment, the method comprises reacting a compound represented by structural formula (II), (II)

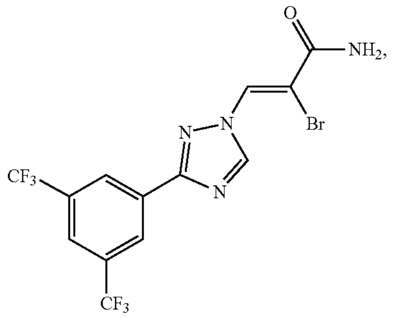

with a compound represented by structural formula (III), (III)

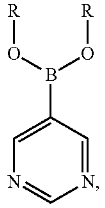

in a first solvent, in the presence of a Pd catalyst and one or more inorganic bases under conditions suitable to prepare a compound represented by structural formula (VII), wherein: each R is hydrogen, a $C_1$-$C_4$ alkyl, or two groups R, taken together with the oxygen atoms to which they are attached, form a 5-7 member cyclic acetal moiety, and thereby obtaining the compound represented by structural formula (VII).

In a $2^{nd}$ aspect, the one or more inorganic base is selected from a quaternary ammonium, sodium, potassium, or cesium carbonate, bicarbonate, acetate, or hydroxide. The remainder of the values and example values of the $1^{st}$ example embodiment are as defined above with respect to the $1^{st}$ aspect.

In a $3^{rd}$ aspect, the Pd catalyst is selected from chloro{[4-(N,N-dimethylamino)phenyl]di-t-butylphosphino}(2'-amino-1,1'-biphenyl-2-yl)palladium(II) or chloro(crotyl)[di-tert-butyl(4-dimethylaminophenyl)phosphine]palladium (II). The remainder of the values and example values of the $1^{st}$ example embodiment are as defined above with respect to their respective $1^{st}$ through $2^{nd}$ aspects.

In a $4^{th}$ aspect, the compound represented by structural formula (III) is a compound represented by structural formula (IIIB):

(IIIB)

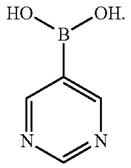

The remainder of the values and example values of the $1^{st}$ example embodiment are as defined above with respect to their respective $1^{st}$ through $3^{rd}$ aspects.

In a $5^{th}$ aspect, the inorganic base is $Cs_2CO_3$ or CsOH, for example, $Cs_2CO_3$. The remainder of the values and example values of the $1^{st}$ example embodiment are as defined above with respect to their respective $1^{st}$ through $4^{th}$ aspects.

In a $6^{th}$ aspect, the Pd catalyst is chloro(crotyl)[di-tert-butyl(4-dimethylaminophenyl)phosphine]palladium(II). The remainder of the values and example values of the $1^{st}$ example embodiment are as defined above with respect to their respective $1^{st}$ through $5^{th}$ aspects.

In a $7^{th}$ aspect, the first solvent is an ether solvent, a C1-C4 alcohol, or a combination thereof. For example, the first solvent is selected from MTBE, CPME, THF, dioxane, MeTHF, methanol, either alone or in combination with water or ethanol. The remainder of the values and example values of the $1^{st}$ example embodiment are as defined above with respect to their respective $1^{st}$ through $6^{th}$ aspects.

In an $8^{th}$ aspect, the Pd catalyst load is from 0.5 mol % to 10 mol %. The remainder of the values and example values of the $1^{st}$ example embodiment are as defined above with respect to their respective $1^{st}$ through $7^{th}$ aspects.

In a $9^{th}$ aspect, an amount of the inorganic base is from 0.5 to 2 molar equivalents of base with respect to the compound represented by structural formula (II). The remainder of the values and example values of the $1^{st}$ example embodiment are as defined above with respect to their respective $1^{st}$ through $8^{th}$ aspects.

In a $10^{th}$ aspect, the conditions suitable to prepare the compound represented by structural formula (VII) comprise:

the Pd catalyst load from 0.5 mol % to 3 mol %;

an amount of the compound represented by structural formula (III) of from 1.0 to 2.2 molar equivalents with respect to the compound represented by structural formula (II);

an amount of the inorganic base of 0.8-1.2 total molar equivalents of base with respect to the compound represented by structural formula (II);

the first solvent comprises from 16 parts to 21 parts of dioxane and from 2 parts to 3 parts of water;

a reaction temperature from about 55° C. to about 60° C.; and a reaction time of about 7-8 hours.

The remainder of the values and example values of the $1^{st}$ example embodiment are as defined above with respect to their respective $1^{st}$ through $9^{th}$ aspects.

In an $11^{th}$ aspect, the method further comprises a step of preparing the compound represented by structural formula (II), (II)

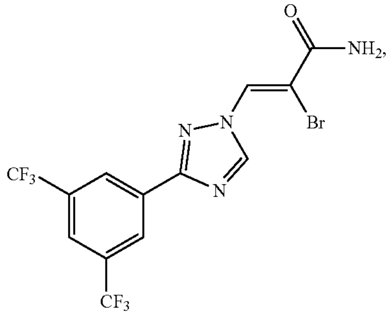

by dehydrobrominating a compound represented by structural formula (IV), (IV)

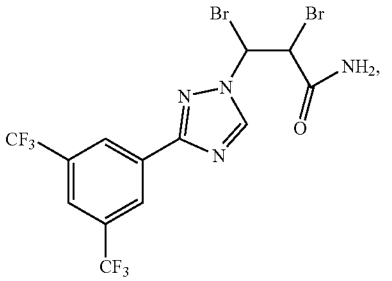

in a second solvent, in the presence of an organic base, under conditions suitable for producing the compound represented by structural formula (II). The remainder of the values and example values of the 1$^{st}$ example embodiment are as defined above with respect to their respective 1$^{st}$ through 10$^{th}$ aspects.

In a 12$^{th}$ aspect, the organic base is triethylamine or diisopropylethylamine (DIPEA). The remainder of the values and example values of the 1$^{st}$ example embodiment are as defined above with respect to their respective 1$^{st}$ through 11$^{th}$ aspects.

In a 13$^{th}$ aspect, the second solvent comprises acetonitrile (ACN). The remainder of the values and example values of the 1$^{st}$ example embodiment are as defined above with respect to their respective 1$^{st}$ through 12$^{th}$ aspects.

In a 14$^{th}$ aspect, the second solvent is 80% ACN/20% water. The remainder of the values and example values of the 1$^{st}$ example embodiment are as defined above with respect to their respective 1$^{st}$ through 13$^{th}$ aspects.

In a 15$^{th}$ aspect, the method further comprises a step of preparing the compound represented by structural formula (IV), (IV)

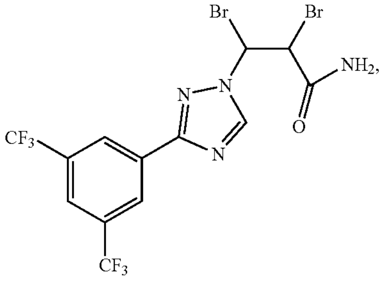

by reacting a compound represented by structural formula (V), (V)

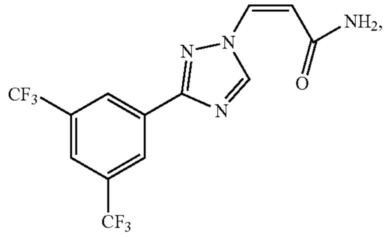

with bromine ($Br_2$) in a third solvent, in the presence of a bromide salt, under conditions suitable to prepare the compound represented by structural formula (IV). The remainder of the values and example values of the 1$^{st}$ example embodiment are as defined above with respect to their respective 1$^{st}$ through 14$^{th}$ aspects.

In a 16$^{th}$ aspect, the third solvent comprises water and the bromide salt is sodium bromide. The remainder of the values and example values of the 1$^{st}$ example embodiment are as defined above with respect to their respective 1$^{st}$ through 15$^{th}$ aspects.

In a 17$^{th}$ aspect, the second solvent comprises about 11 parts of ACN and about 4 parts of $H_2O$ with respect to the compound represented by structural formula (IV), the organic base is DIPEA, and wherein the conditions suitable for preparing the compound represented by structural formula (II) comprise:

- an amount of DIPEA of about 1 molar equivalent with respect to the compound represented by structural formula (IV);
- a reaction temperature of from 20° C. to 25° C.; and
- a reaction time from 2 to 3 hours.

The remainder of the values and example values of the 1$^{st}$ example embodiment are as defined above with respect to their respective 1$^{st}$ through 16$^{th}$ aspects.

In an 18$^{th}$ aspect, the third solvent is acetic acid. The remainder of the values and example values of the 1$^{st}$ example embodiment are as defined above with respect to their respective 1$^{st}$ through 17$^{th}$ aspects.

In a 19$^{th}$ aspect, reacting the compound represented by structural formula (V) with $Br_2$ is performed at a temperature of from 20° C. to 30° C., for a time of from 12 hours to 16 hours. The remainder of the values and example values of the 1$^{st}$ example embodiment are as defined above with respect to their respective 1$^{st}$ through 18$^{th}$ aspects.

In a 20$^{th}$ aspect, the method further comprises a step of preparing a compound represented by structural formula (V), (V)

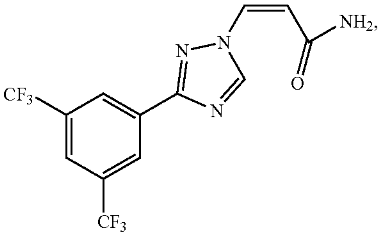

by amidating a compound represented by structural formula (VI), (VI)

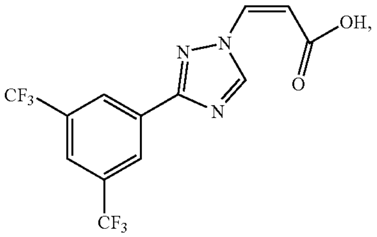

in a fourth solvent, with an amidating agent, in the presence of a tertiary amine organic base and a chloroformate, under conditions suitable for producing the compound represented by structural formula (V). The remainder of the values and example values of the 1st example embodiment are as defined above with respect to their respective 1st through 19th aspects.

In a 21st aspect, the amidating agent is ammonium hydroxide, the tertiary amine organic base is N-methylmorpholine (NMM) and the chloroformate is isobutyl chloroformate represented by the following structural formula

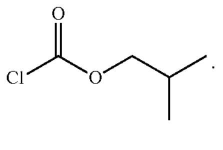

The remainder of the values and example values of the 1st example embodiment are as defined above with respect to their respective 1st through 20th aspects.

In a 22nd aspect, the fourth solvent is tetrahydrofuran (THF) or 2-methyltetrahydrofuran (MeTHF). The remainder of the values and example values of the 1st example embodiment are as defined above with respect to their respective 1st through 21st aspects.

In a 23rd aspect, the fourth solvent is MeTHF, and wherein amidating the compound represented by structural formula (VI) is performed at a temperature from 0° C. to 5° C. and for a time from 3 hours to 4 hours. The remainder of the values and example values of the 1st example embodiment are as defined above with respect to their respective 1st through 22nd aspects.

In a 2nd example embodiment, the present invention is a compound represented by the following structural formula (V)

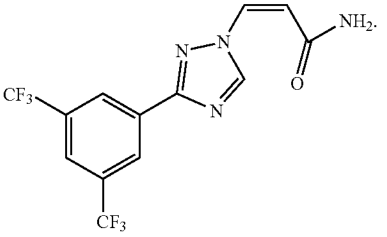

or a salt thereof.

Crystalline Forms I and II of a Compound Represented by Structural Formula (VII) and Recrystallization Methods:

It is to be understood that the term "about", when referring to a numerical value for temperature, means that the numerical value has a range±5° C. of the recited numerical value, unless specified otherwise. For example, when a described embodiment or a claim recites a temperature of "about 20° C.", this is to be understood to mean 20° C.±5° C., that is, a temperature from 15° C. to 25° C.

It is to be understood that the term "about", when referring to a numerical value for time, means that the numerical value has a range±5 minutes of the recited numerical value, unless specified otherwise. For example, when a described embodiment or a claim recites a period of time of "about 60 minutes", this is to be understood to mean 60 minutes±5 minutes, that is, a period of time from 55 minutes to 65 minutes.

It is to be understood that the term "about", when referring to a numerical value for an alcohol-to-water volume ratio, means that the numerical value for x has a range±5% of the recited numerical value, unless specified otherwise. For example, when a described embodiment or a claim recites an alcohol-to-water volume ratio of "about 70/30", this is to be understood to mean an alcohol-to-water volume ratio from 75/25 to 65/35.

Provided herein are crystalline forms of the compound of Structural Formula (VII), designated crystalline Form I and crystalline Form II.

"Crystalline" or "crystal," as used herein, refers to a homogeneous solid formed by a repeating, three-dimensional pattern of atoms, ions or molecules (e.g., an anhydrous molecule or a salt thereof, solvate thereof, or combination of the foregoing) having fixed distances between constituent parts. The unit cell is the simplest repeating unit in this pattern.

The crystalline forms provided herein can be identified on the basis of characteristic peaks in an x-ray powder diffraction (XRPD) analysis. XRPD is a scientific technique that measures the x-rays, neutrons or electrons scattered by a powder or microcrystalline material as a function of scattering angle. XRPD can be used to identify and characterize crystalline solids, as the diffraction pattern produced by a particular solid is typically distinctive to that solid and can be used as a "fingerprint" to identify that solid. For example, an XRPD pattern or diffractogram (e.g., a pattern or diffractogram produced by a sample, such as an unknown sample) that is substantially in accordance with a reference XRPD pattern or diffractogram can be used to determine the identity between the sample material and the reference material. Both the position and the relative intensity of the peaks in an XRPD diffractogram are indicative of the particular phase and identity of a material.

A crystalline form provided herein can be a sole crystalline form or can comprise a mixture of two or more different crystalline forms. For example, in some embodiments, crystalline Form I of the compound represented by Structural Formula (VII) is provided as a sole crystalline form. Alternatively, in other embodiments, a crystalline form can comprise a mixture of two or more crystalline forms of the compound represented by Structural Formula (VII).

"Single crystalline form," as used herein, refers to a single crystal of a crystalline solid or a plurality of crystals of a crystalline solid wherein each of the plurality of crystals has the same crystal form.

Figure 20:
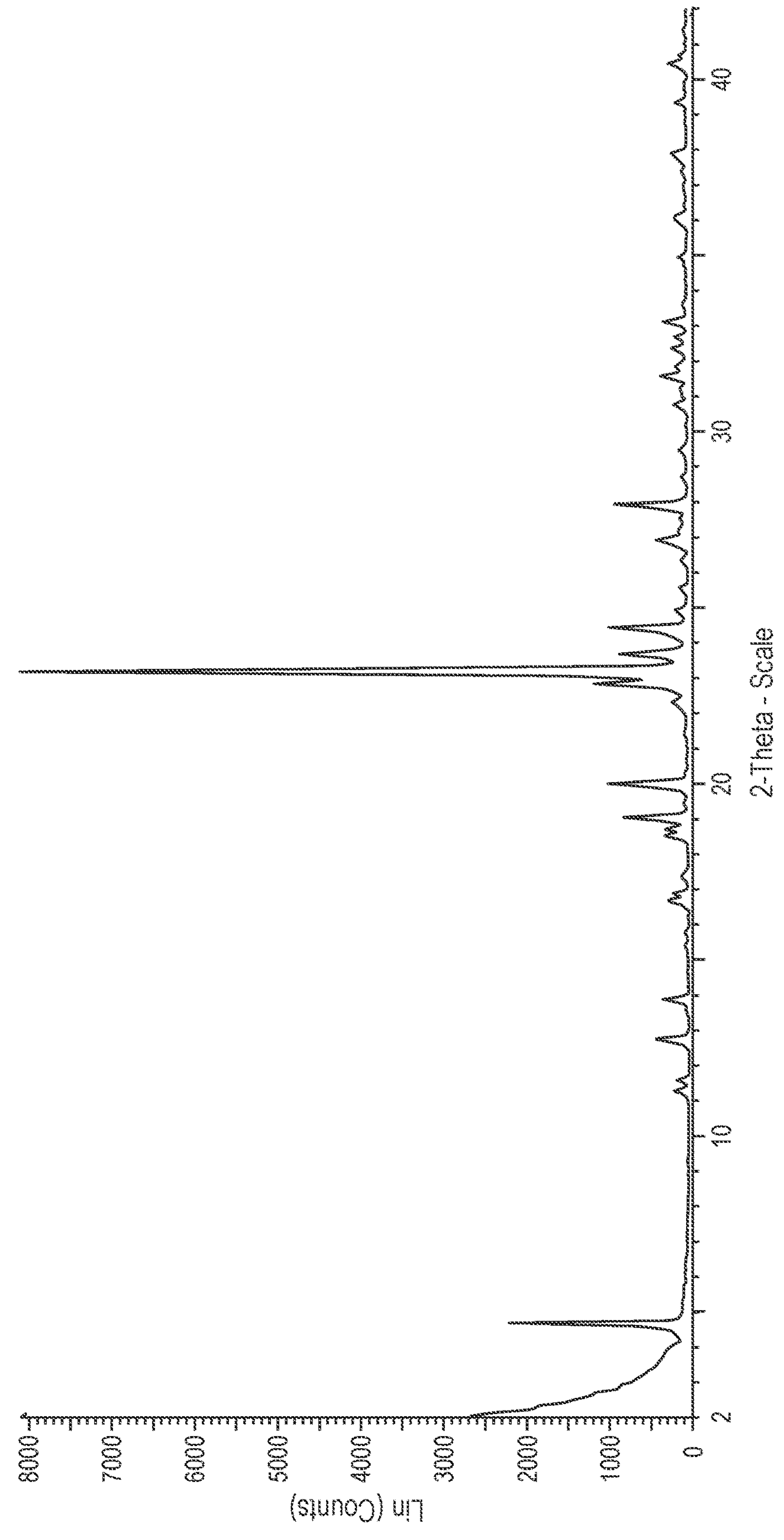
FIG. 20 is an x-ray powder diffraction (XRPD) pattern of the crystalline Form I of compound MB6 (5).
Figure 24:
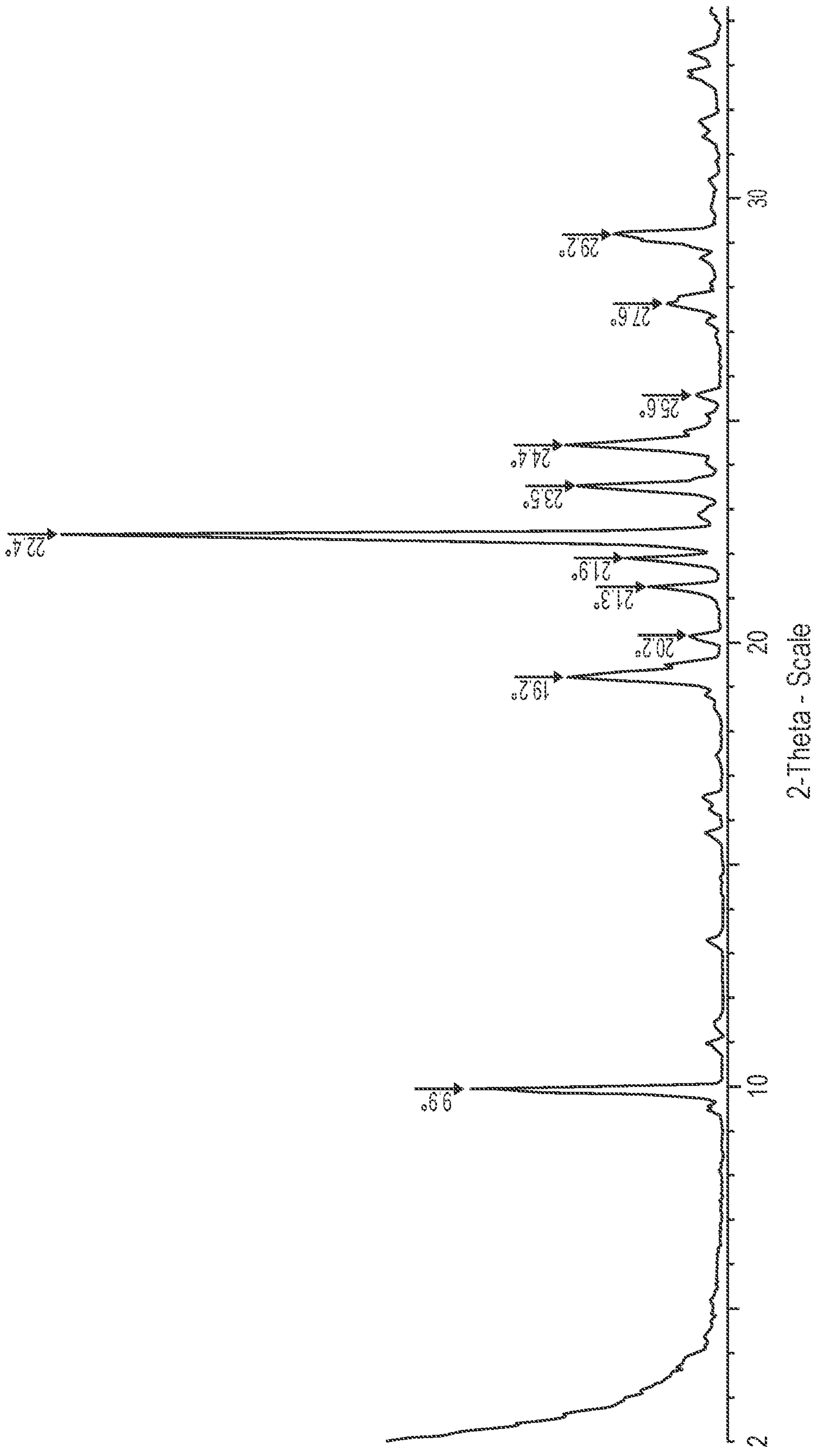
FIG. 24 is an XRPD pattern of the crystalline Form II of compound MB6 (5).

FIGS. 20 and 24 show XRPD patterns of the crystalline Forms I and II, respectively as described herein. An XRPD pattern that is "substantially in accordance" with one or more figures herein showing an XRPD pattern or diffractogram is an XRPD pattern that would be considered by one skilled in the art to represent the same crystalline form of the compound represented by Structural Formula (VII) as the sample of the compound represented by Structural Formula (VII) that provided the XRPD pattern of one or more figures provided herein. Thus, an XRPD pattern that is substantially in accordance may be identical to that of one of the figures or, more likely, may be somewhat different from one or more of the figures. An XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern of the sample and the corresponding XRPD pattern disclosed herein.

It is to be understood that any 2θ angle specified herein means the specified value±0.2°. For example, when a described embodiment or a claim specifies a 2θ of 4.4°, this is to be understood to mean 4.4°±0.2°, that is, a 2θ angle of from 4.2° to 4.6°.

The crystalline Form I and crystalline Form II provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition.

TGA is a method of thermal gravimetric analysis in which changes in physical and chemical properties of a material are measured as a function of increasing temperature (with constant heating rate) or as a function of time (with constant temperature and/or constant mass loss). TGA can provide information about physical phenomena, such as second-order phase transitions, or about chemical phenomena, such as desolvation and/or decomposition.

Figure 21:
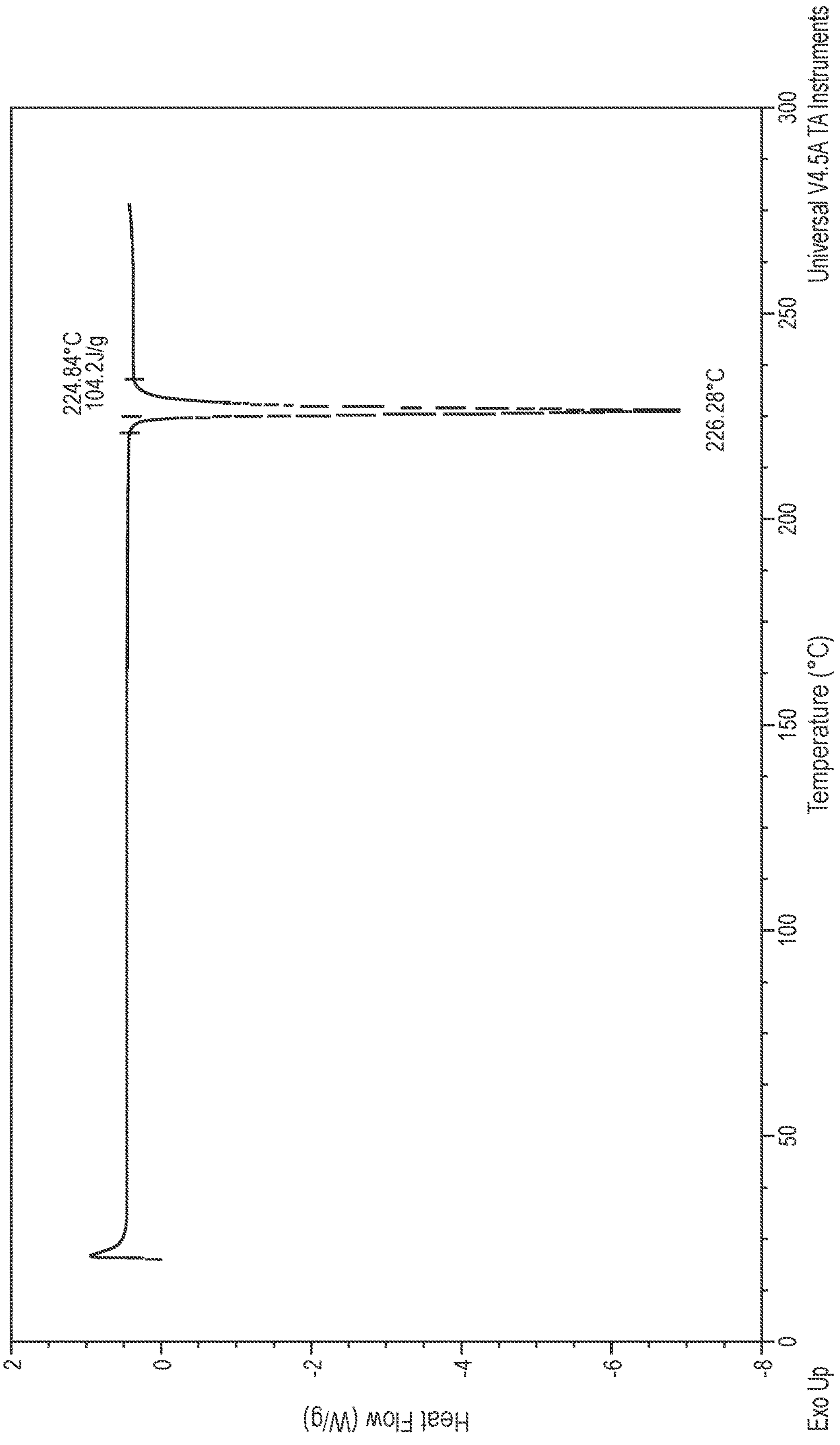
FIG. 21 is a graph depicting a differential scanning calorimetry (DSC) thermogram of the crystalline Form I of compound MB6 (5).
Figure 25:
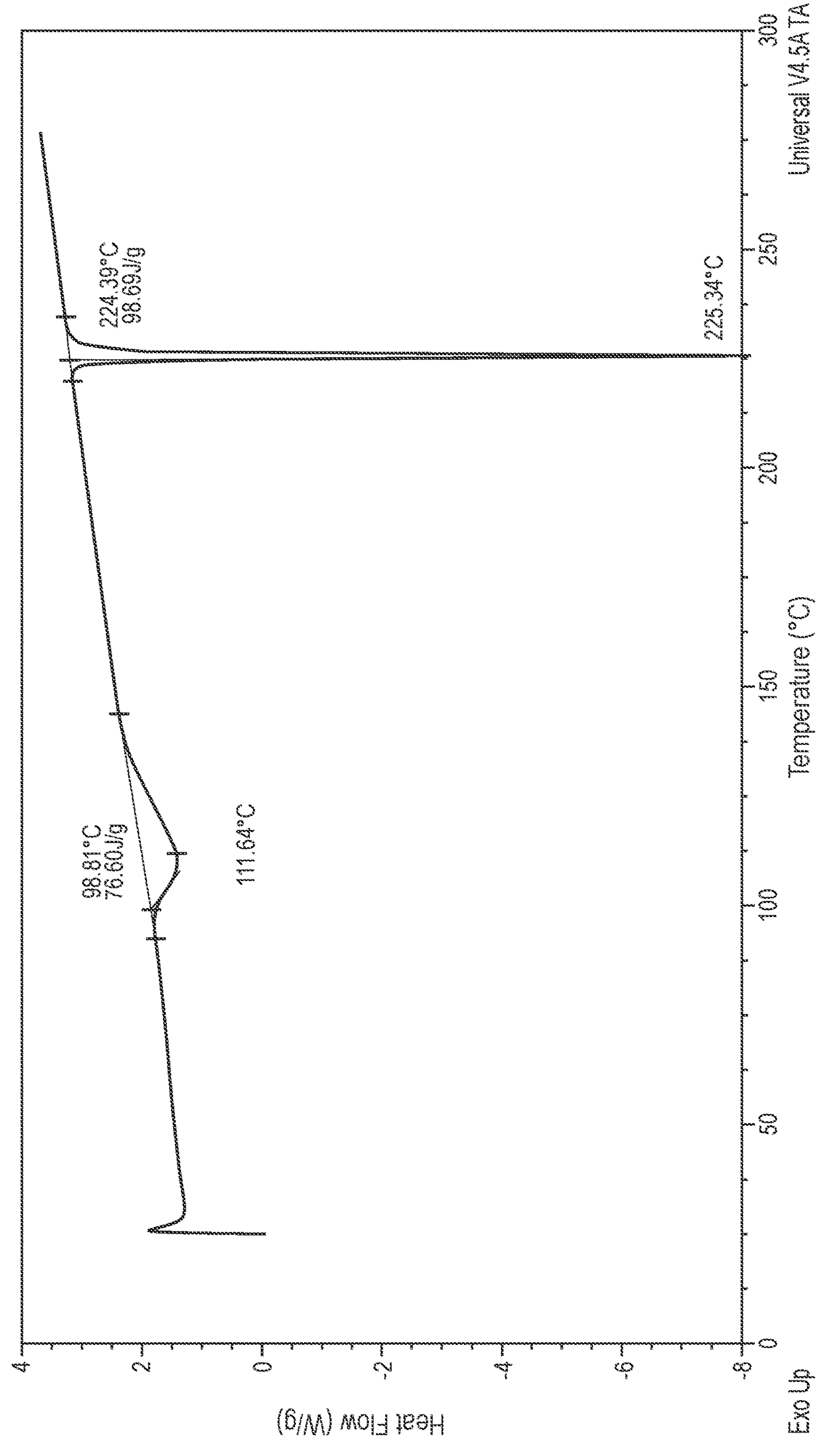
FIG. 25 is a graph depicting a DSC thermogram of the crystalline Form II of compound MB6 (5).

FIGS. 21 and 25 show DSC thermograms of the crystalline Forms I and II, respectively as described herein. A DSC or TGA thermogram that is "substantially in accordance" with one or more figures herein showing a DSC or TGA thermogram is a DSC or TGA thermogram that would be considered by one skilled in the art to represent the same crystalline form of the compound represented by Structural Formula (VII) as the sample of the compound represented by Structural Formula (VII) that provided the DSC or TGA thermogram of one or more figures provided herein.

It is to be understood that any temperature associated with DSC or TGA specified herein means the specified value±5° C. or less. For example, when an embodiment or a claim specifies an endothermic peak at about 184° C., this is to be understood to mean 184° C.±5° C. or less, that is a temperature of from 179° C. to 189° C. In preferred embodiments, a DSC or TGA temperature is the specified value±3° C., in more preferred embodiments, ±2° C.

The crystalline Form I provided can be additionally characterized by dynamic vapor sorption (DVS), wherein a sample is subjected to varying conditions of humidity and temperature, and the response of the sample is measured gravimetrically. The result of a DVS analysis particularly can be a dual curve providing sample weight percent as a function of relative humidity (RH) over time, a dual curve providing sample water content as a function of RH over time, a curve providing weight percent in relation to RH, or a curve providing water content in relation to RH. Equipment useful for measuring such data is known in the art, and any such equipment can be used to measure the compounds according to the present disclosure. In certain embodiments, DVS analysis can be carried out by scanning at a series of specific RH values. Thus, specific polymorphs according to the disclosure may be identified and described in relation to the representative graph and/or the approximate peaks obtained in DVS analysis, particularly scanning from 0% to 95% RH with a step interval of 5% or 10% RH.

Figure 23:
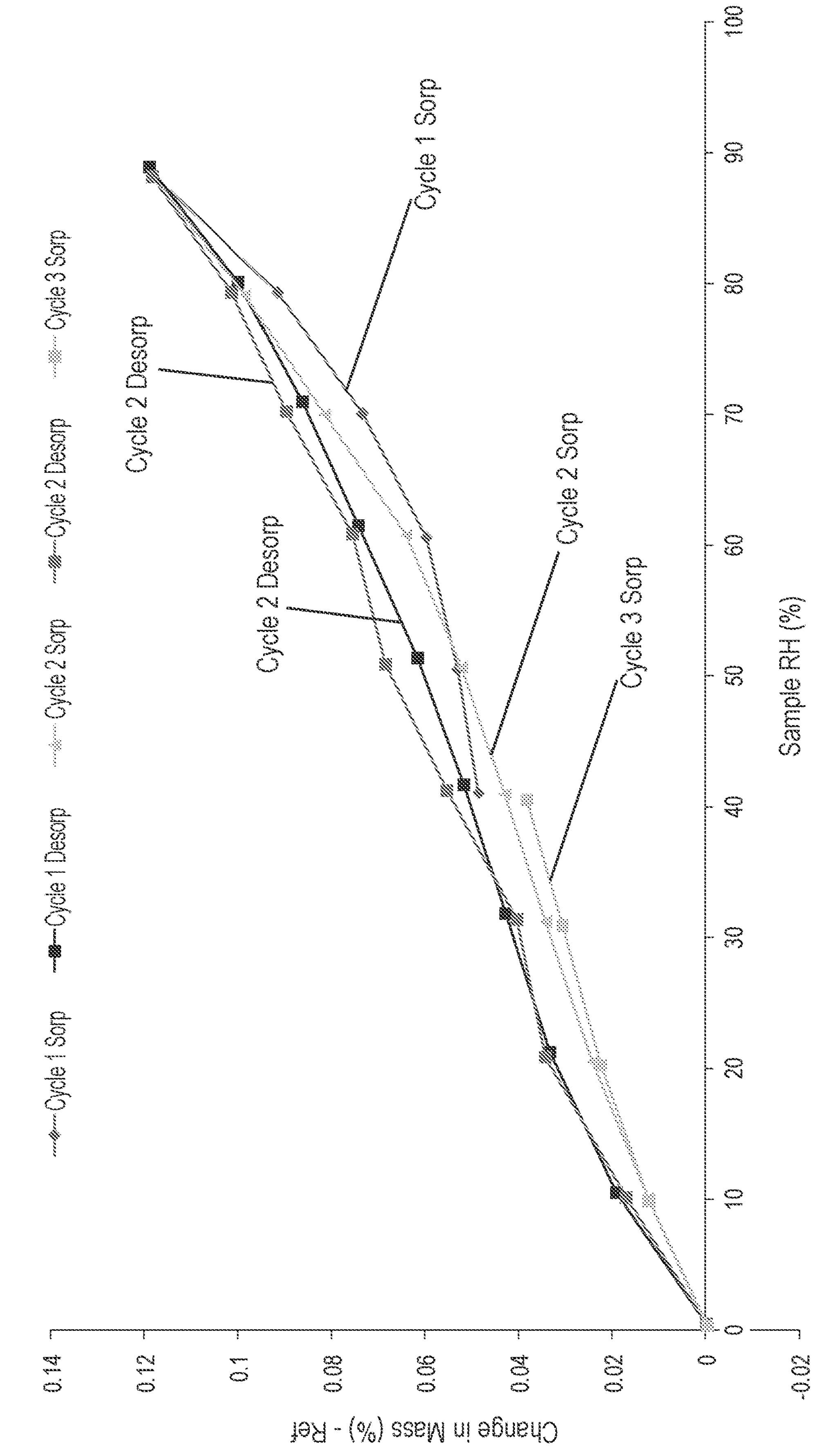
FIG. 23 is a dynamic vapor sorption (DVS) pattern of the crystalline Form I of compound MB6 (5).

FIG. 23 shows a DVS pattern of the crystalline Form I described herein. A DVS pattern that is "substantially in accordance" with one or more figures herein showing a DVS patterns is a DVS pattern that would be considered by one skilled in the art to represent the same crystalline form of the compound represented by Structural Formula (VII) as the sample of the compound represented by Structural Formula (VII) that provided the DVS pattern of one or more figures provided herein.

In some embodiments, crystalline forms provided herein may be crystalline forms of the compound represented by the compound represented by Structural Formula (VII), wherein the compound is in the form of a solvate. "Solvate," as used herein, refers to a chemical compound formed by the interaction of a solute (e.g., a compound of Structural Formula (VII) and one or more solvents (e.g., methanol, ethanol, water). Thus, "solvate" includes solvates containing a single type of solvent molecule and solvates containing more than one type of solvent molecule (mixed solvates or co-solvates). Typically, the one or more solvents in solvates described herein is an organic solvent or a combination of organic solvents, although water can also form solvates, called hydrates.

Form I

In a third example embodiment, the present invention is a crystalline form of the compound represented by Structural Formula (VII), wherein the crystalline form is Form I, and is characterized by x-ray powder diffraction peaks at 2θ angles of 4.6°, 22.8°, 23.2°, and 24.4°; by at least four x-ray powder diffraction peaks at 2θ angles selected from 4.6°, 20.0°, 22.8°, 23.2°, and 24.4°; or by at least five x-ray powder diffraction peaks at 2θ angles selected from 4.6°, 19.0°, 20.0°, 22.8°, 23.2°, 23.7°, 24.4°, and 27.9°. In some aspects of the third example embodiment, crystalline Form I is characterized by an x-ray powder diffraction pattern substantially in accordance with that depicted in FIG. 20.

Figure 22:
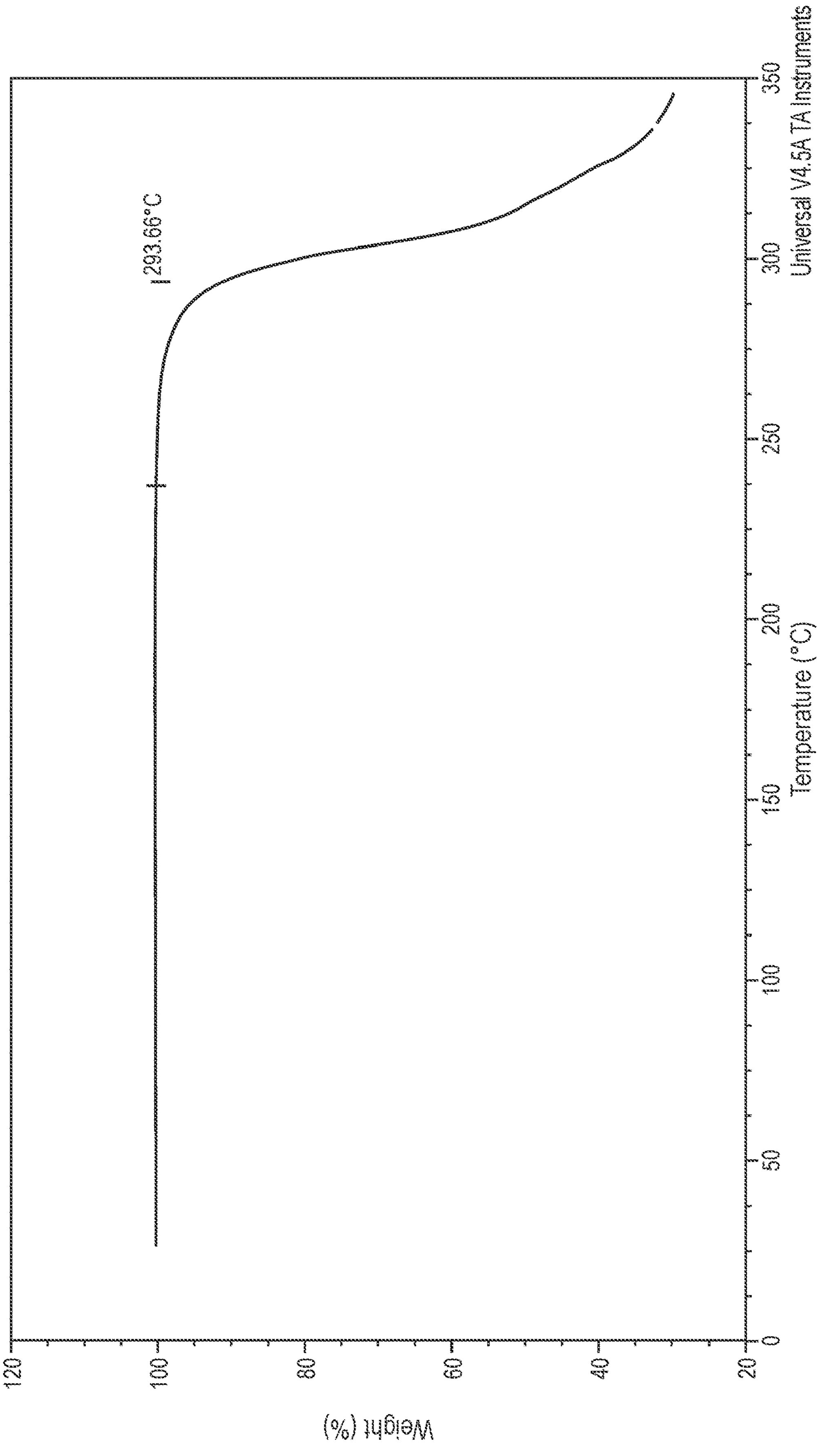
FIG. 22 is a graph depicting a thermogravimetric analysis (TGA) thermogram of compound MB6 (5).

Crystalline Form I may be further characterized by a differential scanning calorimetry thermogram comprising a sharp endothermic peak at about 225° C., consistent with melting. In some aspects of the third embodiment, the DSC thermogram is substantially in accordance with that in FIG. 21. In some aspects of the third embodiment, the TGA thermogram is substantially in accordance with that in FIG. 22.

Crystalline Form I can be additionally characterized by dynamic vapor sorption pattern demonstrating reversible 0.12% w/w water adsorption from 0 to 90% RH. In some aspects of the third embodiment, the DVS pattern is substantially in accordance with that shown in FIG. 23.

Form II

In a fourth example embodiment, the present invention is a crystalline form of the compound represented by Structural Formula (VII), wherein the crystalline form is Form II, and is characterized by x-ray powder diffraction peaks at 2θ angles of 9.9°, 19.2°, 22.4°, and 24.4°; by at least four x-ray powder diffraction peaks at 2θ angles selected from 9.9°, 19.2°, 22.4°, 23.5°, and 24.4°; or by at least five x-ray powder diffraction peaks at 2θ angles selected 9.9°, 19.2°, 21.3°, 21.9°, 22.4°, 23.5°, 24.4°, and 29.2°. In some aspects of the fourth embodiment, crystalline Form VI is characterized by an x-ray powder diffraction pattern substantially in accordance with that depicted in FIG. 24.

Figure 26:
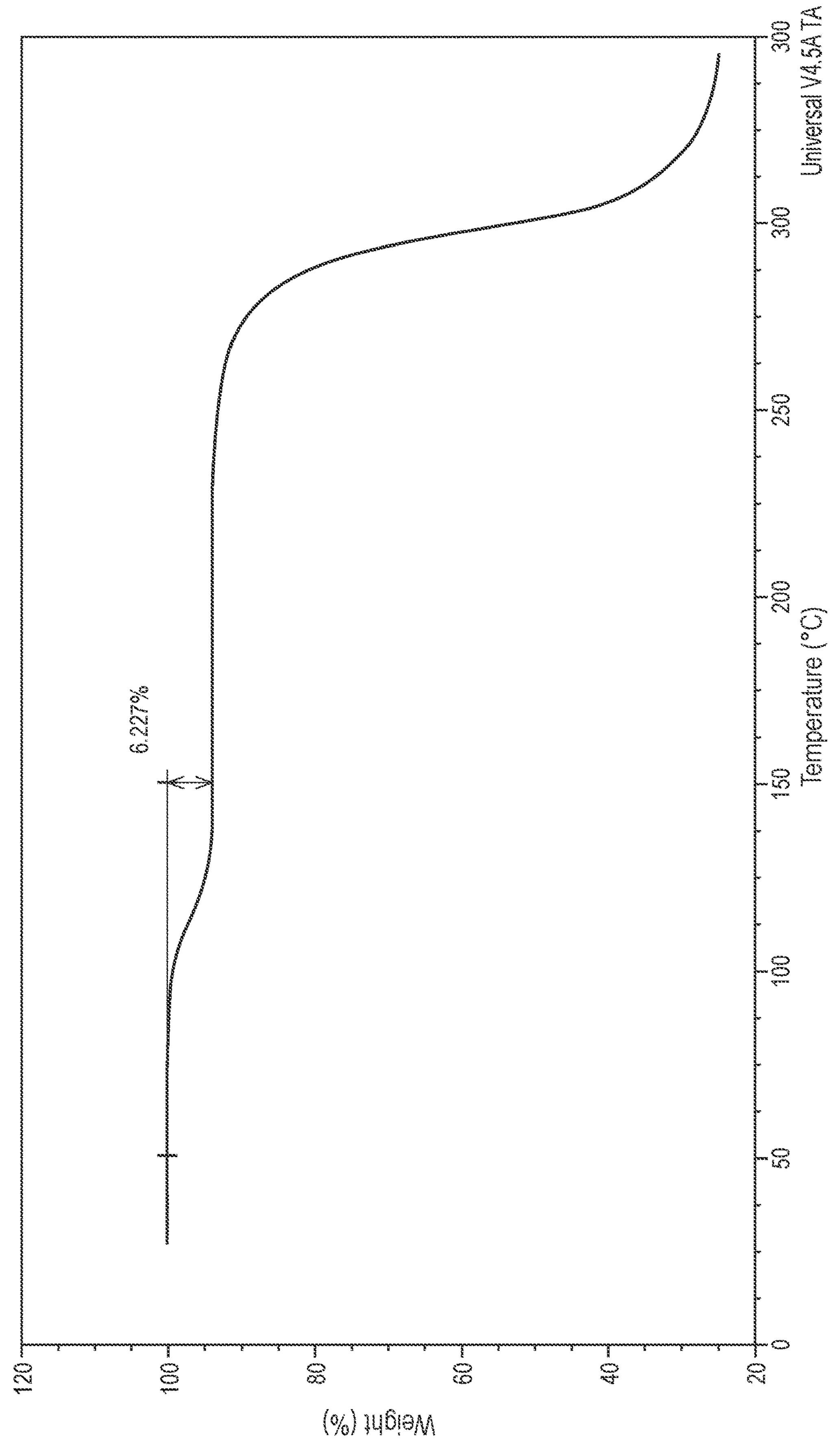
FIG. 26 is a graph depicting a TGA thermogram of the crystalline Form II of compound MB6 (5).

Crystalline Form II may be further characterized by a differential scanning calorimetry thermogram comprising a broad endothermic peak at about 112° C., consistent with desolvation, and a sharp endothermic peak at about 225° C., consistent with melting. In some aspects of the fourth embodiment, the DSC thermogram is substantially in accordance with that in FIG. 25. In some aspects of the fourth embodiment, the TGA thermogram is substantially in accordance with that in FIG. 26.

Crystalline Form II may be a crystalline form of the compound represented by the compound represented by Structural Formula (VII), wherein the compound is in the form of a solvate. For example, the compound of Structural Formula (VII) is a methanol solvate.

Recrystallization Procedure to Isolate Form I:

In a fifth example embodiment, the present invention is a method of preparing crystalline Form I of the compound represented by Structural Formula (VII)

(VII)

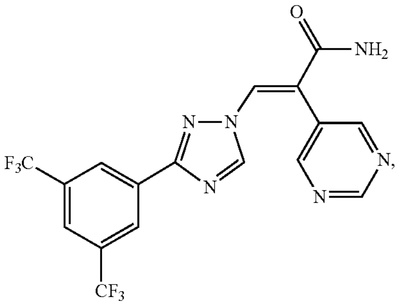

the method comprising: (a) contacting crystalline Form II of the compound represented by Structural Formula (VII) with about 18 volumes of 4-methyl-2-pentanone (MIBK) to form a mixture; (b) heating the mixture of step (a) to about 80-85° C. to form a heated mixture; (c) optionally adding to the heated mixture of step (b) SiDMT; (d) maintaining the heated mixture at a temperature of about 80-85° C. for about 4.5 hours; (e) filtering the heated mixture to obtain a filtrate; (f) adding MIBK at a temperature of about 80-85° C. to the filtrate; (g) inducing nucleation of Form I in the filtrate by cooling the filtrate to about 20-25° C.; (h) crystallizing Form I by a controlled cooling crystallization of the filtrate with a final temperature of 0-5° C.; and (i) isolating crystalline Form I from the filtrate. In one aspect, isolating the crystalline Form I from the filtrate is done by filtration.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

As used herein, "an ether solvent" is an organic solvent that includes a C—O—C moiety. Examples include: Tert-Amyl ethyl ether, Cyclopentyl methyl ether (CPME), Di-tert-butyl ether, Di(propylene glycol) methyl ether, Dibutyl ether, Diethyl ether, Diisopropyl ether, Dimethoxyethane, Dimethoxymethane, 1,4-Dioxane (dioxane), Ethyl tert-butyl ether, Methoxyethane, 2-(2-Methoxyethoxy)ethanol, Methyl tert-butyl ether (MBTE), Morpholine, Polyethylene glycol, Propylene glycol methyl ether, Tetrahydrofuran (THF), 2-Methyl-THF (MeTHF), Tetrahydrofurfuryl alcohol, Tetrahydropyran, 2,2,5,5-Tetramethyltetrahydrofuran.

The term "alkyl," as used herein, unless otherwise indicated, means straight or branched saturated monovalent hydrocarbon radicals, typically $C_1$-$C_{12}$, preferably $C_1$-$C_6$. As such, "$C_1$-$C_6$ alkyl" means a straight or branched saturated monovalent hydrocarbon radical having from one to six carbon atoms (e.g., 1, 2, 3, 4, 5 or 6). Examples of alkyl groups include, but are not limited to, methyl, ethyl, propyl, isopropyl, and t-butyl.

The term "alkoxy," as used herein, means an "alkyl-O—" group, wherein alkyl is defined above. Examples of alkoxy include methoxy and ethoxy.

As used herein, the term "alkenyl" means a saturated straight chain or branched non-cyclic hydrocarbon having from 2 to 12 carbon atoms and having at least one carbon-carbon double bond. Alkenyl groups may be optionally substituted with one or more substituents. The term "alkenyl" or any of its structural depiction encompasses radicals having carbon-carbon double bonds in the "cis" and "trans" or, alternatively, the "E" and "Z" configurations. If an alkenyl group includes more than one carbon-carbon double bond, each carbon-carbon double bond is independently a cis or trans double bond, or a mixture thereof.

The term "amino," as used herein, includes mono- and dialkylamino groups, and refers to a chemical moiety having the formula —$N(R)_2$, wherein each R is independently selected from hydrogen and $C_1$-$C_4$ alkyl.

The term "aryl," alone or in combination, as used herein, means a carbocyclic aromatic system containing one or more rings, which may be attached together in a pendent manner or may be fused. In particular embodiments, aryl is one, two or three rings. In one aspect, the aryl has six to twelve ring atoms. The term "aryl" encompasses aromatic radicals such as phenyl, naphthyl, tetrahydronaphthyl, indanyl, biphenyl, phenanthryl, anthryl and acenaphthyl. An aryl group can be optionally substituted as defined and described herein.

The term "halo" or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The term "haloalkyl", as used herein, includes an alkyl substituted with one or more F, Cl, Br, or I, wherein alkyl is defined above.

The term "heteroaryl", as used herein, refers to an aromatic group containing one or more heteroatoms (e.g., one or more heteroatoms independently selected from O, S and N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. In one aspect, heteroaryl has five to fifteen ring atoms and, preferably, 5 or 6 ring atoms. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The foregoing heteroaryl groups may be C-attached or N-attached (where such is possible). For instance, a group derived from pyrrole may be pyrrol-1-yl (N-attached) or pyrrol-3-yl (C-attached).

"Hydroxyl" means —OH.

"Oxo" means =O.

"Sulfhydryl" means —SH.

"Cyano" means —CN.

"Thioalkoxy" and "thioalkyl" means —S-alkoxy and —S-alkyl, respectively wherein alokoxy and alkyl are defined as above.

A "pyrimidinyl" is a radical derived from a pyrimidine ring, whether substituted or unsubstituted

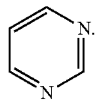

A "dioxane" is a compound represented by the following structural formula

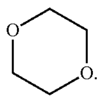

The term "acetal," as used herein, refers to a moiety represented by the following structural formula

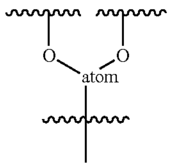

where "atom" means any atom that can form covalent bonds with two oxygen atoms, such as carbon or boron, and the wavy line represent points of attachment to other atoms. A cyclic acetal moiety is an acetal in which the "atom," taken together with the two oxygen atoms attached thereto, forms a cyclic group. An example of a cyclic acetal moieties is a group represented by the following structural formula:

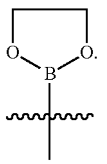

As used herein, an "inorganic base" refers to bases that do not include an organic moiety. Examples include metal ($NH_4^+$, Li, K, Na, K, Rb, Cs, Mg, Ca, Ba, Sr, etc) hydroxides, phosphates, acetates, carbonates and bicarbonates. Additional examples include Na, K, or Cs carbonates or bicarbonates, phosphates, acetates, and hydroxide. A further example of an inorganic base is a quaternary ammonium salt. In some example embodiments, an inorganic base is CsOH or $Cs_2CO_3$.

An "organic base" is an organic base that acts as a base, according to any one of the accepted definitions of a base (Arrhenius, Bronsted or Lewis).

A "Pd catalyst", as used herein, refers to any Pd-containing materials, whether pre-formed or formed in situ by addition of a Pd-containing material and separate ligand, capable of promoting a reaction between compounds represented by structural formulas (II) and (III) that produces a compound represented by structural formula (VII). Examples of such catalysts are a Pd catalyst selected from chloro{[4-(N,N-dimethylamino)phenyl]di-t-butylphosphino}(2'-amino-1,1'-biphenyl-2-yl)palladium(II) or chloro(crotyl)[di-tert-butyl(4-dimethylaminophenyl)phosphine]palladium(II).

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstitued.

Example substituents on any alkyl, aryl or heteroaryl can be selected from the group consisting of —OH, —SH, nitro (—$NO_2$), halogen, amino, cyano, $C_1$-$C_{12}$ alkyl, $C_2$-$C_{12}$ alkenyl, $C_2$-$C_{12}$ alkynyl, $C_1$-$C_{12}$ alkoxy, $C_1$-$C_{12}$ haloalkyl, $C_1$-$C_{12}$ haloalkoxy and $C_1$-$C_{12}$ thioalkoxy. Example substituents on alkyl include the above substituents and oxo. In one embodiment, the substituent is an amino group having the formula —$N(R)_2$, wherein each R is independently selected from hydrogen and $C_1$-$C_4$ alkyl.

Pharmaceutical Compositions

In a sixth example embodiment, the disclosure relates to a pharmaceutical composition, comprising crystalline Form I of the compound represented by Structural Formula (VII) according to any one of the aspects of the third embodiment and a pharmaceutically acceptable carrier. For example, the pharmaceutical composition comprises crystalline Form I of the compound represented by Structural Formula (VII), characterized by x-ray powder diffraction peaks at 2θ angles 4.6°, 22.8°, 23.2°, and 24.4°, and a pharmaceutically acceptable carrier.

The term "pharmaceutically acceptable carrier" means a non-toxic solvent, dispersant, excipient, adjuvant or other material which is mixed with the active ingredient in order to permit formation of a pharmaceutical composition, i.e., a dosage form capable of being administered to a subject. A "pharmaceutically acceptable carrier" should not destroy the activity of the compound with which it is formulated. Pharmaceutically acceptable carriers are well known in the art.

Pharmaceutically acceptable carriers, adjuvants or vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical compositions of the disclosure can be administered orally, parenterally (including subcutaneous, intramuscular, intravenous and intradermal), by inhalation spray, topically, rectally, nasally, buccally, vaginally or via an implanted reservoir. In some embodiments, provided pharmaceutical compositions are administrable orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. In a particular embodiment, the pharmaceutical compositions are administered orally, subcutaneously, intraperitoneally or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutical compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Specific pharmaceutically acceptable carriers suitable for use in an oral formulation such as a tablet or capsule include, but are not limited to, microcrystalline cellulose (Avicel PH101), croscarmellose Sodium (Ac-Di-Sol), kollidon 30 powder (polyvinylpyrrolidone, povidone), colloidal silicon dioxide M5-P, magnesium stearate, microcrystalline cellulose (Avcel PH102), sodium lauryl sulfate (Kolliphor SLS Fine) and Colloidal Silicon Dioxide M5-P. Each of the above listed carriers can be used in an oral formulation either alone or in any combination.

Further pharmaceutically acceptable carriers suitable for use in an oral formulation such as a tablet or capsule include, but are not limited to, microcrystalline cellulose (Avicel PH112), crospovidone (polyplasdone XL-10), colloidal silicone dioxide (Cab-O-Sil M-5P), Talc, starch and calcium stearate.

Pharmaceutical compositions of this disclosure may also be administered by nasal aerosol or inhalation.

The amount of the crystalline Form I of the compound represented by Structural Formula (VII) in pharmaceutical compositions of this disclosure is such that it is effective to measurably treat or prevent disorders associated with CRM1 activity in a subject. The term "subject," as used herein, can be a human subject or an animal.

The amount of the crystalline Form I that can be combined with the pharmaceutically acceptable carrier materials to produce a pharmaceutical composition in a single dosage form will vary depending upon the host treated and/or the particular mode of administration. In one embodiment, the pharmaceutical compositions should be formulated so that a dosage of between 0.01-200 mg of crystalline Form I of the compound represented by Structural Formula (VII) can be administered to a patient receiving these compositions. In another embodiment, the dosage is from about 0.5 to about 100 mg. The dosage can be administered once a day or multiple times per day and can be administered once a week or multiple times per week (for example day1, day3 and day5) over a given treatment cycle.

It should also be understood that a specific dosage and treatment regimen for any particular subject (e.g., patient) will depend upon a variety of factors, including the age, body weight, general health, sex, diet, time of administration, rate of excretion, drug combination, and the judgment of the treating physician and the severity of the particular disease being treated.

Upon improvement of a subject's condition, a maintenance dose of a pharmaceutical composition of this disclosure can be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Method of Treatment and Used for Crystalline Form I and Pharmaceutical Compositions Comprising Same Crystalline Form I of the compound represented by Structural Formula (VII) disclosed herein and pharmaceutical compositions comprising same are generally useful for the inhibition of CRM1 and are, therefore, useful for treating one or more disorders associated with the activity of CRM1. Thus, in a seventh embodiment, the present disclosure provides a method for treating a disorder associated with CRM1 activity, comprising administering to a subject in need thereof a therapeutically effective amount of crystalline Form I or a pharmaceutical composition comprising crystalline Form I and a pharmaceutically acceptable carrier as described herein. Crystalline Form I and pharmaceutical composition comprising same can also be administered to cells in culture, e.g., in vitro or ex vivo, or to a subject, e.g., in vivo, to treat, prevent, and/or diagnose a variety of disorders, including those described hereinbelow.

The activity of crystalline Form I and a pharmaceutical composition comprising same as an inhibitor of CRM1 may be assayed in vitro, in vivo or in a cell line. Detailed conditions for assaying an inhibitor of CRM1, such as crystalline Form I of the compound represented by Structural Formula I, are set forth in International Publication No. WO 14/205389.

The term "treat" or "treating" means to alleviate symptoms, eliminate the causation of the symptoms, either on a temporary or permanent basis, or to prevent or slow the appearance of symptoms of the named disorder or condition.

The term "CRM1-mediated" disorder or condition or "disorder associated with CRM1 activity," as used herein, means any disease or other deleterious condition in which CRM1 is known to play a role. Accordingly, another embodiment of the present disclosure relates to treating or lessening the severity of one or more diseases in which CRM1 is known to play a role. In some embodiments, the present disclosure provides methods of treating a disease associated with expression or activity of p53, p73, p21, pRB, p27, INB, NFNB, c-Abl, FOXO proteins, COX-2, or an HDAC (histone deacetylases) in a subject comprising administering to the subject a therapeutically effective amount of a crystalline Form I described herein. In another embodiment, the present disclosure relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder wherein said method comprises administering to a patient in need thereof a crystalline Form I of a compound represented by Structural Formula (VII) or a pharmaceutical composition comprising Form I and a pharmaceutically acceptable carrier. In a more specific embodiment, the present disclosure relates to a method of treating or lessening the severity of cancer. Specific examples of the above disorders are set forth in detail below.

The term "therapeutically effective amount" means an amount of crystal Form I of the compound represented by Structural Formula (VII) that is effective in treating or lessening the severity of one or more symptoms of a disorder or condition. In the case of promoting wound healing, a therapeutically effective amount is an amount that promotes healing of a wound.

As used herein, the term "prophylaxis" or "prophylactic" refer to measures taken to preventing or increasing resistance to a disease prior to its onset as well as to measures that ameliorate the symptoms of a disease when taken prior to its onset. Prophylaxis also includes measures taken to prevent the recurrence of a disease.

The term "prophylactically effective amount" means an amount of crystal Form I of the compound represented by Structural Formula (VII) that is effective for prophylaxis of a condition treatable by such compound.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

In some embodiments, the present disclosure relates to a method for promoting wound healing in a subject in need thereof, comprising administering to the subject in need thereof a therapeutically effective amount of crystalline Form I of the compound represented by Structural Formula (VII) or a pharmaceutical composition described herein.

Cancers treatable by crystalline Form I of the compound represented by Structural Formula VII or pharmaceutical compositions described herein include, but are not limited to, hematologic malignancies (leukemias, lymphomas, myelomas including multiple myeloma, myelodysplastic syndrome and myeloproliferative disorder) and solid tumors (carcinomas such as prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple. In one embodiment, the cancer is multiple myeloma.

Inflammatory disorders treatable by crystalline Form I of the compound represented by Structural Formula (VII) or pharmaceutical compositions described herein include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by crystalline Form I of the compound represented by Structural Formula (VII) or pharmaceutical compositions described herein include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this disclosure also include chronic viral infections, including hepatitis B and hepatitis C. Additionally, viral diseases treatable by the compounds of this disclosure include infections caused by a coronavirus, e.g., SARS, MERS, and SARS-CoV-2.

Exemplary ophthalmology disorders treatable by crystalline Form I of the compound represented by Structural Formula (VII) or pharmaceutical compositions described herein include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by crystalline Form I of the compound represented by Structural Formula (VII) or pharmaceutical compositions described herein include, but are not limited to, Parkinson's, Alzheimer's, and Huntington's, and Amyotrophic lateral sclerosis (ALS/Lou Gehrig's Disease).

Crystalline Form I of the compound represented by Structural Formula (VII) or pharmaceutical compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Crystalline Form I of the compound represented by Structural Formula (VII) or pharmaceutical compositions described herein may also be used to treat disorders related to food intake such as obesity and hyperphagia.

In another embodiment, crystalline Form I of the compound represented by Structural Formula (VII) or pharmaceutical compositions described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In some embodiments, the disorder or condition associated with CRM1 activity and treatable by crystalline Form I of the compound represented by Structural Formula (VII) is beta-thalassemia, muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospirosis renal disease, glaucoma, retinal disease, ageing, headache, pain, complex regional pain syndrome, cardiac hypertrophy, muscle wasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, Behcet's disease, incontinentia pigmenti, tuberculosis, asthma, Crohn's disease, colitis, ocular allergy, appendicitis, Paget's disease, pancreatitis, periodonitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, Parkinson's disease, multiple sclerosis, Alzheimer's disease, amyotropic lateral sclerosis, Huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present disclosure relates to a use of crystalline Form I of the compound represented by Structural Formula (VII) or pharmaceutical compositions described herein for the manufacture of a medicament for the treatment of a disorder associated with CRM1 activity. The present disclosure also relates to crystalline Form I or pharmaceutical compositions described herein for use in treating a disorder associated with CRM1 activity. Specific examples of disorders associated with CRM1 activity are as set forth in detail herein.

In yet further aspects, the present disclosure relates to a use of crystalline Form I of the compound represented by Structural Formula (VII) or pharmaceutical compositions described herein for the manufacture of a medicament for the treatment of a disease associated with expression or activity of p53, p73, p21, pRB, p27, INB, NFNB, c-Abl, FOXO proteins, COX-2 or an HDAC in a subject. In some embodiments, the present disclosure relates to a use of crystalline form I or pharmaceutical compositions described herein in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

In some embodiments, the present disclosure relates to a method for inhibiting CRM1 in a biological sample comprising contacting the biological sample with, or administering to the patient, crystalline Form I of the compound represented by Structural Formula (VII) or pharmaceutical compositions described herein.

Neoplastic Disorders

Crystalline Form I of the compound represented by Structural Formula (VII) or pharmaceutical compositions described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

Crystalline Form I of the compound represented by Structural Formula (VII) or pharmaceutical compositions described herein are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. Crystalline Form I or pharmaceutical compositions described herein are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome.

Exemplary sarcomas include fibrosarcoma, alveolar soft part sarcoma (ASPS), liposarcoma, leiomyosarcoma, chondrosarcoma, synovial sarcoma, chordoma, spindle cell sarcoma, histiocytoma, rhabdomyosarcoma, Ewing's sarcoma, neuroectodermal sarcoma, phyllodes/osteogenic sarcoma and chondroblastic osteosarcoma.

Metastases of the aforementioned cancers can also be treated or prevented in accordance with the methods described herein.

In various example embodiments, crystalline Form I of the compound represented by Structural Formula (VII), or pharmaceutical compositions described herein can be used for treating a disorder selected from a colorectal cancer, a prostate cancer, myelodysplastic syndrome, an inflammatory bowel disease, a nasopharyngeal cancer, and a penile cancer.

Combination Therapies

In some embodiments, crystalline Form I of the compound represented by Structural Formula (VII) or pharmaceutical compositions described herein are administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents to a subject in need thereof to treat any one or more indications described herein. For example, crystalline Form I or pharmaceutical compositions described herein may be administered with another therapeutic agent simultaneously or sequentially in separate unit dosage forms or together in a single unit dosage form. Accordingly, the present disclosure relates to a single unit dosage form comprising crystalline Form I or pharmaceutical compositions described herein, an additional therapeutic agent, and a pharmaceutically acceptable carrier.

In one embodiment of the disclosure, where a second therapeutic agent is administered to a subject, the effective amount of crystalline Form I of the compound represented by Structural Formula (VII) is less than its effective amount would have been if the second therapeutic agent were not administered. In another embodiment, the effective amount of the second therapeutic agent is less than its effective amount would have been if crystalline Form I of the compound represented by Structural Formula (VII) were not administered. In this way, undesired side effects associated with high doses of either agent may be minimized. Other potential advantages (including without limitation improved dosing regimens and/or reduced drug cost) will be apparent to those of skill in the art. The additional agents may be administered separately from crystalline Form I of the compound represented by Structural Formula (VII) or pharmaceutical compositions described herein, as part of a multiple dose regimen. Alternatively, those agents may be part of a single dosage form, mixed together with crystalline Form I or pharmaceutical compositions described herein.

In certain embodiments, crystalline Form I of the compound represented by Structural Formula (VII) or pharmaceutical compositions described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa. In a specific embodiment, crystalline Form I of the compound represented by Structural Formula (VII) or pharmaceutical compositions described herein are administered in combination with dexamethasone.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiments, crystalline Form I of the compound represented by Structural Formula (VII) or pharmaceutical compositions described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, crystalline Form I of the compound represented by Structural Formula VII or pharmaceutical compositions described herein are administered in combination with an anthracycline or a Topo II inhibitor. In certain embodiments, crystalline Form I of the compound represented by Structural Formula (VII) or pharmaceutical compositions described herein are administered in combination with Doxorubicin (Dox). In certain embodiments, crystalline Form I of the compound represented by Structural Formula (VII) or pharmaceutical compositions described herein are administered in combination with bortezomib (and more broadly including carfilzomib).

Cancer Combination Therapies

In some embodiments, crystalline Form I of the compound represented by Structural Formula (VII) or pharmaceutical compositions described herein, (e.g., in a pharmaceutical composition described herein) are administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors, and anti-angiogenic therapies. Examples of each of these treatments are provided below. As used herein, the term "combination," "combined," and related terms refer to the simultaneous or sequential administration of therapeutic agents in accordance with this disclosure. For example, crystalline Form I of the compound represented by Structural Formula (VII) can be administered with another therapeutic agent simultaneously or sequentially in separate unit dosage forms or together in a single unit dosage form. Accordingly, the present disclosure provides a single unit dosage form comprising the crystalline Form I of the compound represented by Structural Formula (VII), an additional therapeutic agent, and a pharmaceutically acceptable carrier.

The amount of both crystalline Form I of the compound represented by Structural Formula (VII) and additional therapeutic agent (in those pharmaceutical compositions which comprise an additional therapeutic agent as described above) that can be combined with the carrier materials to produce a single dosage form will vary depending upon the host treated and the particular mode of administration. Preferably, pharmaceutical compositions of this disclosure should be formulated so that a dosage of between 0.01-200 of crystalline Form I of the compound represented by Structural Formula (VII) can be administered.

Chemotherapy

In some embodiments, crystalline Form I of the compound represented by Structural Formula (VII) or pharmaceutical compositions described herein are co-administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carfilzomib, Carmofur, Carmustine, Celecoxib, Cetuximab, Chlorambucil, Chlormethine, CHOEP-21, CHOP, Cisplatin, Cladribine, Clofarabine, Crisantaspase, Cyclophosphamide, Cytarabine or ara-C, Dacarbazine, Dactinomycin, DA EPOCH, Daratumumab, Daunorubicin, Decitabine, Demecolcine, Dexamethasone, Docetaxel, Doxorubicin, Efaproxiral, Elesclomol, Elsamitrucin, Enocitabine, Epirubicin, Eribulin, Estramustine, Etoglucid, Etoposide, FLAG (Flu+Cyt), Floxuridine, Fludarabine, Fluorouracil (5FU), FOLFOX, Fotemustine, Gemcitabine, gemcitabine-oxaliplatin (GemOx), Gliadel implants, Hydroxycarbamide, Hydroxyurea, Ibrutinib, Idarubicin, Ifosfamide, Irinotecan, Irofulven, Ixabepilone, Ixazomib, Larotaxel, Lenalidomide, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nab-paclitaxel, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, PLD (pegylated liposomal doxorubicin), Plicamycin, Pomalidomide, Porfimer sodium, Prednimustine, Procarbazine, Raltitrexed, Ranimustine, R-CHOP, r-dhaox, r-dhap, Rituximab, Romidepsin Rubitecan, Sapacitabine, Semustine, Sitimagene ceradenovec, Sorafonib, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Targeted Therapy

Crystalline Form I of the compound represented by Structural Formula (VII) or pharmaceutical compositions described herein can be used in combination with or as a part of a targeted therapy. Targeted therapy constitutes the use of agents specific for the target of interest (e.g., a deregulated protein) in cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a pharmaceutical composition described herein, e.g., Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Process to Prepare the Compound Represented by Structural Formula (VII) (Compound 5)):

Referring to the FIG. 1, an overall reaction scheme of one aspect of the present invention is shown. In Step 1, compound 1 is amidated. In Step 2, two telescoping reactions convert compound 2 into the dibrominated compound 3, followed by a dehydrobromination of 3 into compound 4. In Step 3, compound 5 is produced via a Suzuki coupling between compound 4 and the compound represented by structural formula (IIIB).

Crystalline Forms of the compound represented by Structural Formula (VII) (Compound 5):

Referring to FIGS. 20-26, characterization data for crystalline Forms I and II of the compound represented by Structural Formula (VII) (also referred to herein as Compound 5 or Compound MB6 and referred to in the art as eltanexor or KPT-8602) are shown. Such data includes x-ray powder diffraction (XRPD) patterns, differential scanning calorimetry (DSC) thermograms, thermogravimetric analysis (TGA) thermograms and dynamic vapor sorption (DVS) patterns. A description of how each form is isolated and the techniques used to generate the characterization data are provided below.

General Materials and Methods for Characterization of Crystalline Forms

XRPD

Per USP guidelines, variable hydrates and solvates may display peak variances greater than 0.2° 2θ and therefore peak variances of 0.2° 2θ are not applicable to these materials.

"Prominent Peaks" are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks." In general, the more data collected to determine Representative Peaks, the more confident one can be of the classification of those peaks.

"Characteristic peaks," to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample was exposed to the X-ray beam for 120 seconds. The software used for data collection was GADDS for XP/2000 4.1.43 and the data were analyzed and presented using Diffrac Plus EVA v15.0.0.0.

Ambient conditions: Samples were prepared as flat plate specimens using powder as received without grinding. Approximately 1-2 mg of the sample was lightly pressed on a glass slide to obtain a flat surface.

Non-ambient conditions: Samples run under non-ambient conditions were mounted on a silicon wafer with heat-conducting compound. The sample was then heated to the appropriate temperature at 20° C./min and subsequently held isothermally for 1 minute before data collection was initiated.

Additionally, X-ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.6.1 and the data were analyzed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2θ;

Step size: 0.05° 2θ;

Collection time: 0.5 s/step.

TGA

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminium DSC pan and heated at 10° C./min from ambient temperature to 350° C. A nitrogen purge at 60 ml/min was maintained over the sample.

The instrument control software was Advantage for Q Series v2.5.0.256 and Thermal Advantage v5.5.3 and the data were analyzed using Universal Analysis v4.5A.

DSC

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 280° C. A purge of dry nitrogen at 50 ml/min was maintained over the sample.

The instrument control software was Advantage for Q Series v2.8.0.394 and Thermal Advantage v5.5.3 and the data were analysed using Universal Analysis v4.5A.

DVS

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min. The relative humidity (RH) was measured by a calibrated Rotronic probe (dynamic range of 1.0-100% RH), located near the sample. The weight change, (mass relaxation) of the sample as a function of % RH was constantly monitored by the microbalance (accuracy±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

TABLE 1

| Method for SMS DVS Intrinsic experiments | |
|---|---|
| Parameter | Value |
| Adsorption - Scan 1 | 40-90 |
| Desorption, Adsorption - Scan 2 | 90-0, 0-40 |
| Desorption / Adsorption - Scan 3 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

The sample was recovered after completion of the isotherm and re-analyzed by XRPD.

$^1$H NMR

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2012.

Process:

Step 1

Step 1 involves the preparation of the acrylamide represented by the chemical structure referenced as KPT-9508/MB3 in FIG. 1. Isobutylchloroformate is used to generate the mixed anhydrides that are then quenched in ammonium hydroxide to provide MB3/KPT-9508. The details of the reaction scheme are as follows:

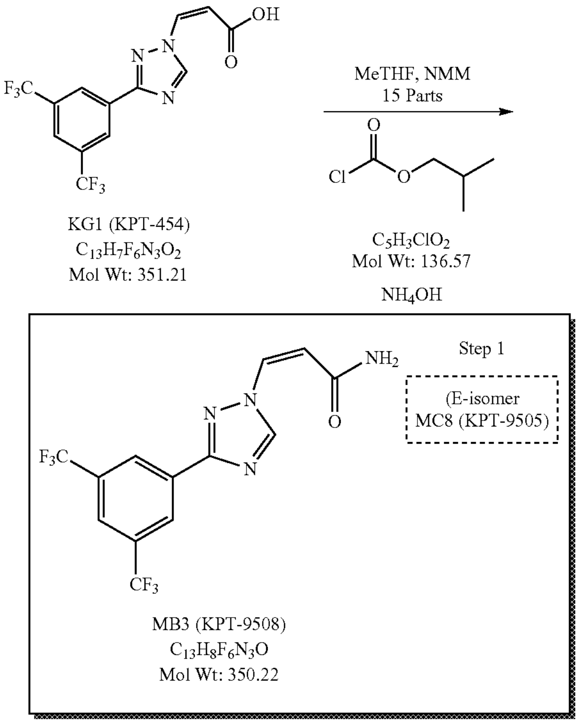

KG1 (KPT-454)
$C_{13}H_7F_6N_3O_2$
Mol Wt: 351.21

$C_5H_3ClO_2$
Mol Wt: 136.57

MB3 (KPT-9508)
$C_{13}H_8F_6N_3O$
Mol Wt: 350.22

To a 558 L glass lined conical bottom vessel equipped with sulfuric acid scrubber and inerted under nitrogen was charged ammonium hydroxide (29.653 kg 26% w/w aqueous solution) and the solution temperature adjusted to 0-5° C. (internal temperature 8.4° C. to 3.0° C. for 11 hours 36 minutes).

A separate 206 L glass lined vessel, inerted under nitrogen was charged with 2-MeTHF (24.0 kg) which was heated at reflux for 30 minutes to dry the glass vessel and condenser assembly. The vessel and contents were adjusted to <30° C., then the 2-MeTHF sampled for IPC (the first sample showed residual water of 0.2% w/v with a target of <0.1% w/v so the reflux was repeated with additional 2-MeTHF). The vessel was drained and then dried under vacuum.

To the 206 L vessel was charged KG1 (KPT-454, 15.5 kg), and 2-MeTHF (77.1 kg), then the batch was agitated and adjusted to 0-5° C. (internal temperature 15.5° C. to 0.7° C. over 15 minutes) to form a solution. The subsequent additions of isobutyl chloroformate and N-methyl morpholine followed by quenching in ammonium hydroxide required completion within a maximum of 4 hours (actual time 3 hours 5 minutes). Isobutyl chloroformate (12.1 kg) was charged while maintaining a temperature of 0-5° C. (temperature range of 0.0° C. to 1.0° C. for 25 minutes) and the addition equipment rinsed forward with 2-MeTHF (8.1 kg). N-methyl morpholine (8.9 kg, pre-cooled to 4-8° C.) was charged while maintaining a temperature of 0-5° C. (temperature range 0.4° C. to 5.6° C. over 25 minutes) and the addition equipment rinsed forward with 2-MeTHF (5.4 kg). The batch was agitated for a period of 30-45 minutes (35 minutes, internal temperature 1.8° C. to 0.5° C.).

While maintaining a temperature of 0-5° C., the batch was transferred to the first vessel containing ammonium hydroxide with vigorous agitation, while maintaining a temperature of 0-10° C. in the receiving vessel (temperature range of 0.1° C. to 9.1° C. over a range of 40 minutes). The reaction mixture from the second vessel was rinsed into the first vessel with 2-MeTHF (13.1 kg), agitated for 30 minutes at 4.3° C., and then sampled for IPC (Residual KG1+KG5 wrt MB3+MC8 was 2% a/a with target of NMT 2% a/a). The batch was then adjusted to a temperature of 20-25° C. (53 minutes, internal temperature 1.7° C. to 20.4° C.). Agitation was stopped for 49 minutes to allow for phase separation and the lower aqueous phase was drained and discarded (separation time 58 minutes, interface with organic layer, upper organic phase 140 L, lower aqueous phase 20 L). Water (77.5 kg) was charged while maintaining a temperature of 20-25° C. (temperature range 22.2° C. to 24.3° C. for 40 minutes), and agitated for 20 minutes. Agitation was then stopped for 45 minutes to allow for phase separation and the lower aqueous phase was drained and discarded (separation time 35 minutes, interface with aqueous layer, upper organic phase 144 L, lower aqueous phase 86 L).

The batch was cooled to 0-5° C. (from 22.5° C. to 3.3° C. for 65 minutes) and placed under vacuum, then gradually warmed to a temperature of 17.3° C. and distilled to a target volume of 57-62 L (visual volume 61 L, dip volume measured at 57 L) over 3 hours 10 minutes. N-heptane (10.5 kg) was charged over 30 minutes at a temperature of 20.7° C. to 21.7° C., then agitated for 1 hour to crystallize the product. The presence of solids was verified visually, then further n-heptanes (94.9 kg) was charged in 1 hour over a temperature range of 22.2° C. to 22.5° C.

Figure 16:
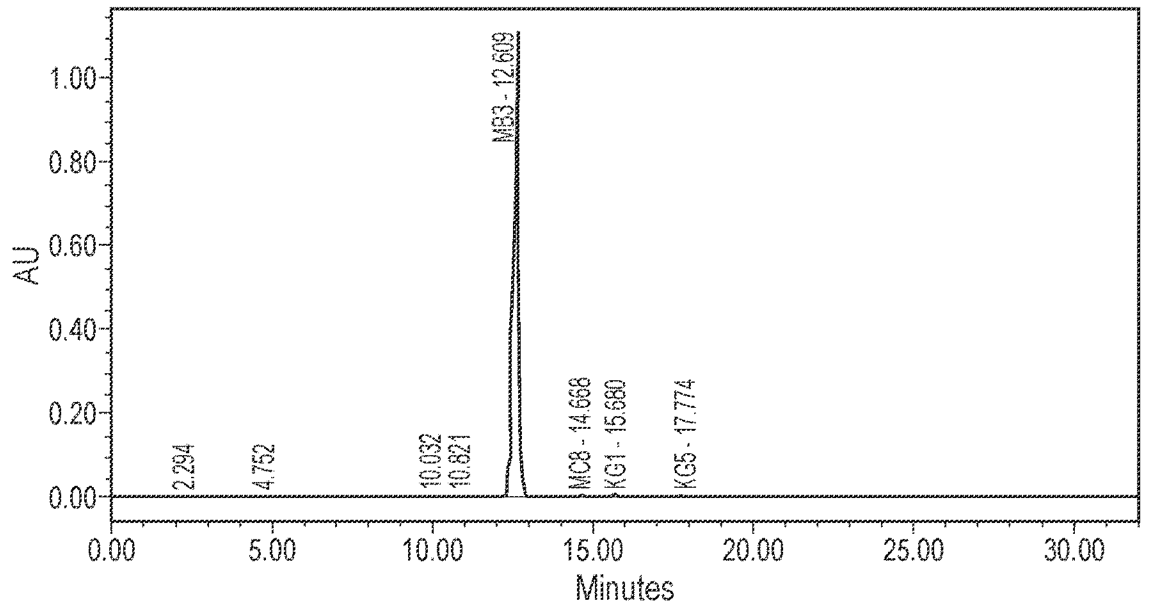
FIG. 16 depicts the HPLC analysis results of the product of Step 1 of the overall reaction.

The batch was isolated by filtration through 20 cfm polyester filter cloth with cotton backing cloth (filtration time of 2 hours 20 minutes held at 22.5° C. on SRF filter), then the filtrate was returned to the vessel and re-filtered over 1 hour and 24 minutes at 22.2° C. to rinse forward the remaining solids. The filter cake was washed with n-heptane (21.2 kg in two portions—filtration times of 15, and 17 minutes), then de-liquored (2 hours) and dried under a stream of nitrogen (58 hours, ambient temperature). IPC analysis showed the LOD to be 1.4% w/w at 58 hours with a limit of NMT 5% w/w, and the product was packaged to provide 12.4 kg, 80% yield of KPT-9508. The isolated product conformed to the HPLC standard for this compound. The HPLC of the product is shown in FIG. 16.

The HPLC conditions were as follows:

Apparatus:

1. UPLC column: Agilent Zorbax SB-CN, 3.0×100 mm. 1.8 μm
2. Detector: 260 nm
3. Column temp: 50° C.
4. Mobile phase: A: 0.1% TFA in H20
   B: 50% ACN: 45% MeOH: 5% H20
5. Flow rate: 0.5 ml/min
6. Injection volume: 5 μL
7. Run time: 32 minutes
8. Gradient:

| Time (min) | % A | % B |
|---|---|---|
| 0.0 | 75 | 25 |
| 5.0 | 75 | 25 |
| 21.0 | 55 | 45 |
| 22.0 | 30 | 70 |
| 28.0 | 30 | 70 |
| 28.1 | 75 | 25 |
| 32.0 | 75 | 25 |

9. Dissolution Solvent (DS): 75% ACN: 25% $H_2O$+0.1% TFA
10. Purge solvent: 50% ACN: 50% $H_2O$
11. Needle Wash: 50% ACN: 50% $H_2O$
12. Thermo Scientific 'Targer' all-plastic disposable Luer-Lok syringe, 3 ml or equivalent (must be compatible with ACN/$H_2O$ DS)
13. 0.2 μm PTFE filter
14. BECTON DICKINSON & CO. (8-D) prepackaged needle or equivalent Reagents and Standards:

1. Acetonitrile (ACN), Methanol (MeOH), Water ($H_2O$), HPLC grade or equivalent
2. Trifluoroacetic Acid (TFA), reagent grade or equivalent
3. MB3 Resolution Standard: 1393-ES-038-1 (Contain Unk-1-0.04%, MC8=10%, KG1=0.4%, KG5:0.4%) or equivalent.

Figure 18:
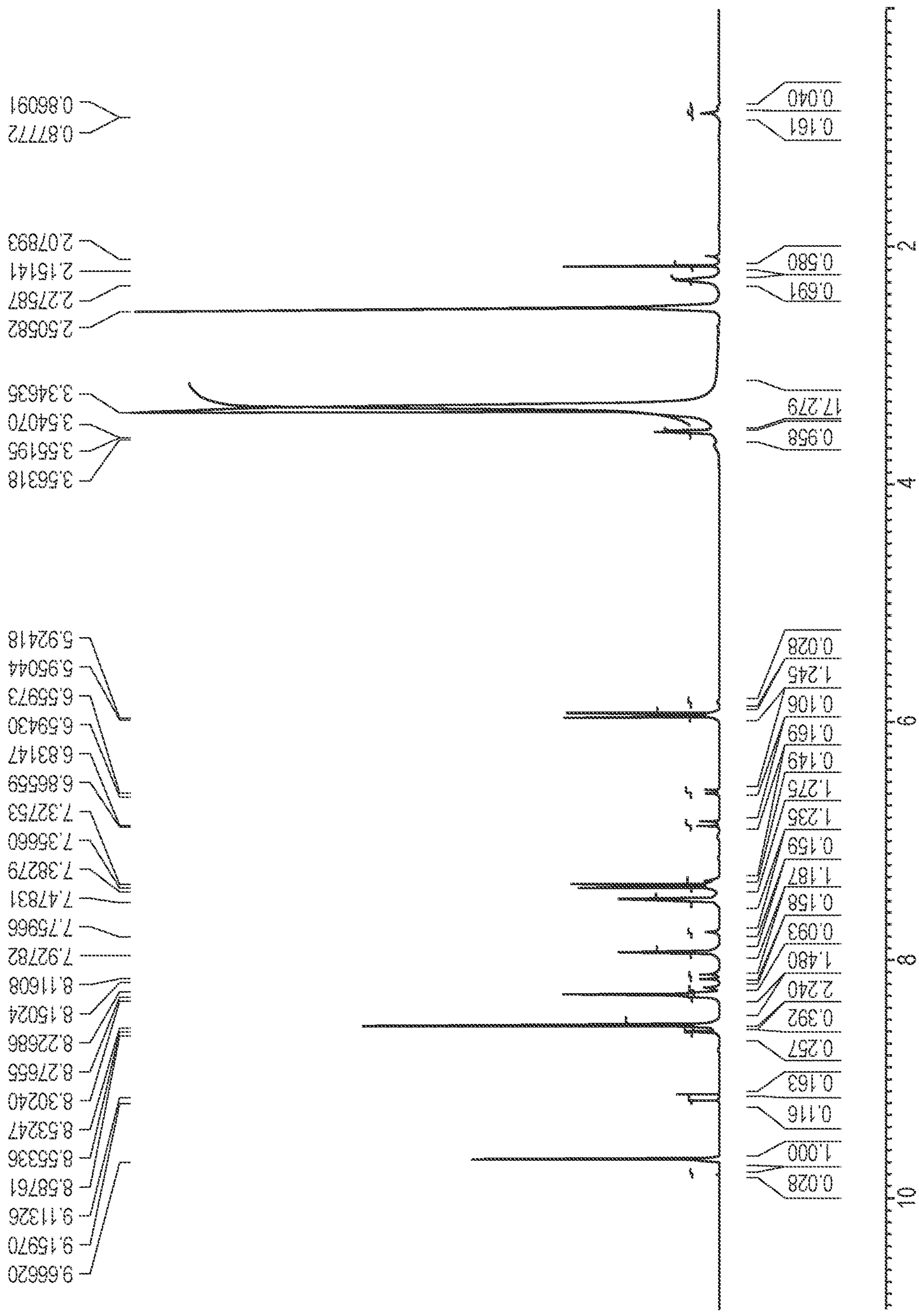
FIG. 18 shows a $^{1}H$ NMR spectrum of compound MB3 (see FIG. 1).

The $^1H$ NMR spectrum of the final product (KPT-9508/MB3) is shown in FIG. 18.

Step 2

Step 2 consists of two telescoped conversions to form the dibrominated mixture of isomers ME2/KPT-9515+ME3/KPT-9506 (Step 2a of FIG. 1) which is then dehydrobrominated to form the intermediate mixture of isomers MB5/KPT-7538+MB9/KPT-9507 (Step 2b of FIG. 1).

Step 2a Scheme

Step 2a Scheme

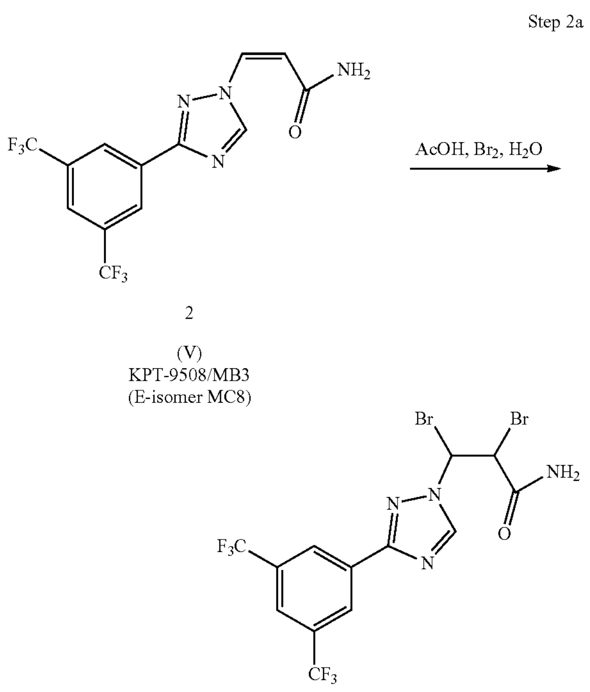

2

(V)

KPT-9508/MB3

(E-isomer MC8)

3

(IV)

ME2, ME3 (KPT-9515, KPT-9506)

In a 2 L three-neck round bottom flask fitted with overhead agitation, thermometer, addition funnel and nitrogen bubbler was charged 14.69 g of NaBr and 110 mL of acetic acid. The contents of the batch were agitated at ambient temperature. The batch was charged with 45.6 g of bromine. The addition funnel was rinsed forward with 110 mL of acetic acid. In a separate 500 mL three-neck flask was charged 55 g of MB3 and 220 mL of acetic acid. The contents of the 500 mL flask were agitated at ambient temperature to form a solution.

The contents of the 500 mL vessel were charged via addition funnel into the 2 L vessel over a period of 1 hour while maintaining the internal temperature in the range of 20-30° C. The addition funnel was rinsed forward with 110 mL of acetic acid. The batch was further agitated at 20-30° C. for a minimum period of 16 hours.

The batch was charged with 275 mL of 10% w/v sodium bisulfite solution over a minimum period of 30 minutes while maintaining an internal temperature of 20-30° C. The batch was charge with 275 mL of water over a period of 5 minutes while maintaining an internal temperature of 20-30° C. The batch was further agitated at 20-30° C. for a minimum period of 60 minutes. An aliquot of the batch in removed and observed for the presence of residual bromine. The complete reduction of bromine was observed by the presence of a white to off-white suspension.

The contents of the batch were then filtered through Whatmann paper (70 mm) on a Buchner funnel under reduced pressure. The filter cake was washed with 220 mL of water in two approximately equal portions. The collected cake was maintained under reduced pressure for a minimum period of 15 minutes at 20-30° C. The intermediate ME2 product was obtained with a crude mass of 102.13 g and HPLC purity against developed standards of ME2: 86.0% a/a and ME3: 9.5% a/a.

Step 2b Scheme

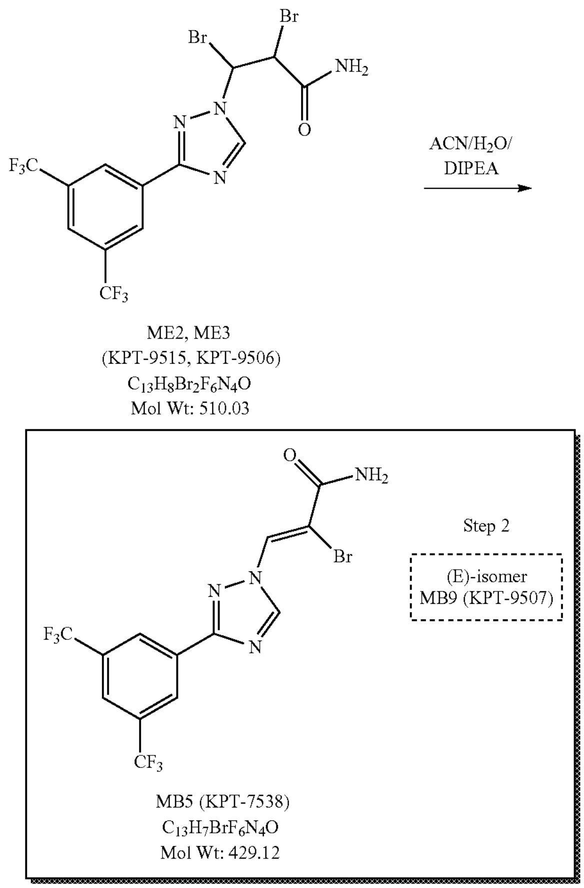

ME2, ME3
(KPT-9515, KPT-9506)
$C_{13}H_8Br_2F_6N_4O$
Mol Wt: 510.03

MB5 (KPT-7538)
$C_{13}H_7BrF_6N_4O$
Mol Wt: 429.12

The reaction procedure described for Step 2b provides an improvement to earlier development work which presented difficulties with sampling of the reaction mixture during in-process control (IPC) testing. The difficulties with IPC testing was largely a result of the excessive thickness of the reaction mixture of Step 2b. The difficulties were addressed by using diisopropylethylamine rather than trimethylamine as the base, increasing the mixture volume by about 3-fold and using a mixture of water and acetonitrile rather than acetonitrile alone. The final procedure that was discovered to address the noted difficulties is described below.

A 500 mL three neck round bottom flask was equipped with a thermometer, overhead stirrer and nitrogen inlet. The flask was charged with 25 g of ME2 (49 mmol; 1.0 eq.) and 140 mL of ACN (8 parts with respect (wrt) to MB3) and 70 mL of water (4 parts with respect to MB3). To a separate 100 mL round-bottom flask was charged 8.6 mL of DIPEA (49 mmol, 1.0 eq. wrt MB3) and 52 mL of ACN (3 parts wrt MB3). The mixture was agitated for 20-30 minutes. With vigorous agitation, the DIPEA solution was added portion wise to the suspension of ME2 over a period of 1.0 to 1.5 hours. The addition assembly was rinsed forward with 9 mL of ACN (0.5 parts wrt MB3). The batch was agitated for 2-3 hours at 20-25° C. IPC testing was performed and the IPC target was met (target: residual ME2 wrt MB5 is no more than (NMT) 0.3% a/a).

The resulting suspension was filtered using filter paper. The filter cake was washed with 34 mL of 8:2 ACN/$H_2O$ mixture (2 parts wrt MB3). The filter cake was washed with 34 mL of ACN (2 parts wrt MB3). The filter cake was dried by nitrogen purge with aspirator suction for 20 hours. The isolated product was a white solid and the purity was assessed by HPLC under the following protocol:

Apparatus:

1. UPLC column: Agilent Zorbax SB-CN, 3.0×100 mm, 1.8 μm
2. Detector: 260 nm
3. Column temp: 50° C.
4. Mobile phase: A: 0.1% TFA in $H_2O$
   B: 50% ACN: 45% MeOH: 5% $H_2O$
5. Flow rate: 0.5 ml/min
6. Injection volume: 4 μL
7. Run time: 35 minutes
8. Gradient:

| Time (min) | % A | % B |
|---|---|---|
| 0.0 | 75 | 25 |
| 5.0 | 75 | 25 |
| 21.0 | 55 | 45 |
| 25.0 | 30 | 70 |
| 30.0 | 30 | 70 |
| 31.0 | 75 | 25 |
| 35.0 | 75 | 25 |

9. Dissolution Solvent (DS): DMSO
10. Purge solvent: 50% ACN: 50% $H_2O$
11. Needle Wash: 50% ACN: 50% $H_2O$
12. Thermo Scientific 'Targer' all-plastic disposable Luer-Lok syringe, 3 ml or equivalent (must be compatible with ACN/$H_2O$ DS)
13. 0.2 μm PTFE filter
14. BECTON DICKINSON & CO. (B-D) prepackaged needle or equivalent Reagents and Standards:

1. Acetonitrile (ACN), Dimethylsulfoxide (DMSO), Methanol (MeOH), Water ($H_2O$), HPLC grade or equivalent
2. Trifluoroacetic Acid (TFA), reagent grade or equivalent.
3. KG1 impurity standard: 03-STD-061 or equivalent
4. KG5 impurity standard: 1267-0-101-1 or equivalent.
5. MB3 impurity standard: 1393-ES-038-1 or equivalent
6. ME2 impurity standard: 1389-NN-130-1 or equivalent
7. ME3 impurity standard: KP9506-C-1-A or equivalent
8. MB5 Resolution Standard: 1389-NN-174-1 (Contain Unk-1=0.14%, MC8=0.13%, MB9=3.4%) or equivalent.

Figure 17:
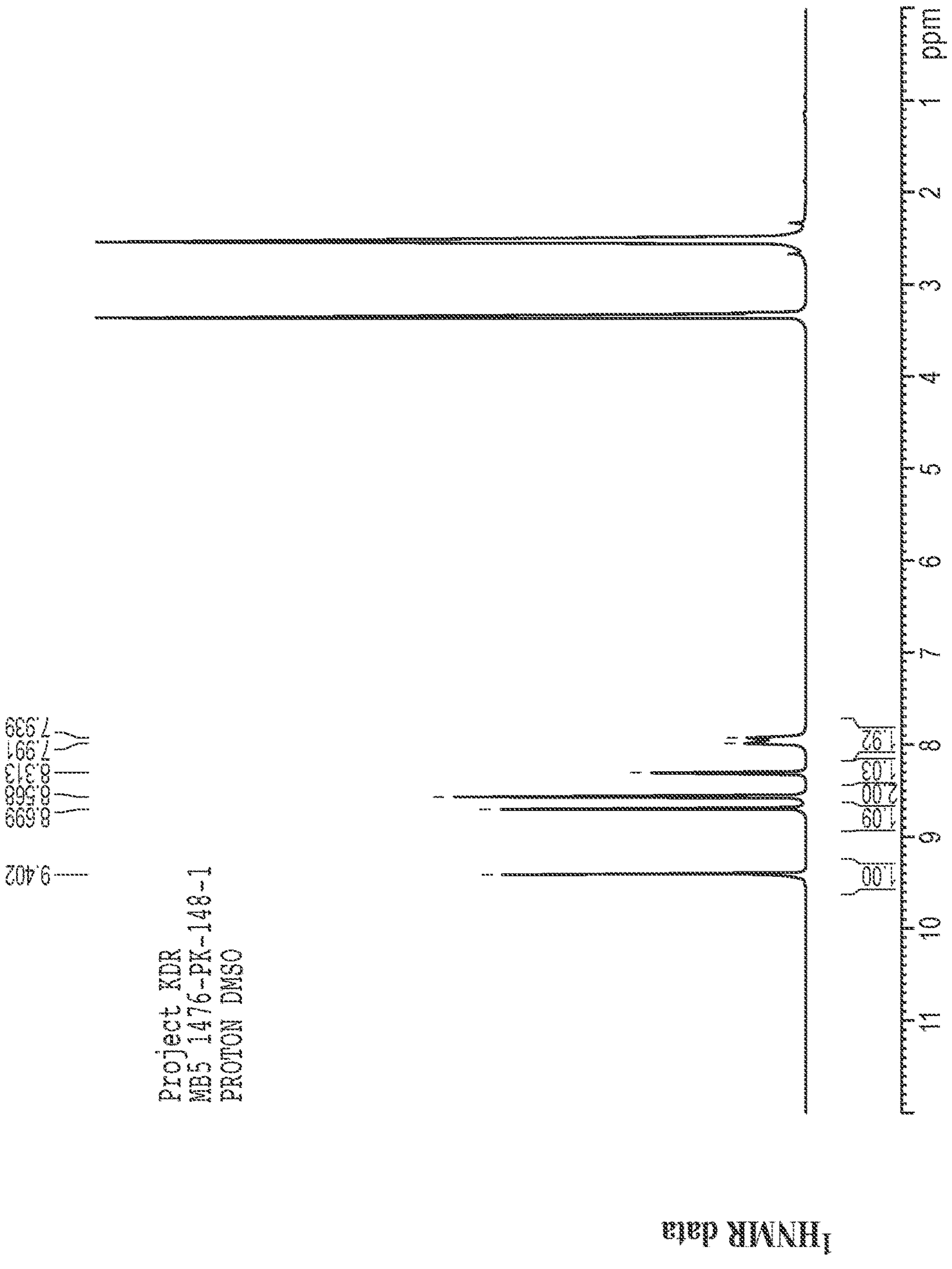
FIG. 17 shows a proton NMR in DMSO of the batch of the product of Step 2 of the overall reaction.

Duplicate runs resulted in isolated yields of 86.0% and 90.7% having 99.2% a/a and 99.2% a/a respectively. A proton NMR in DMSO of the batch isolated at the 86.0% yield is shown in FIG. 17.

Step 3

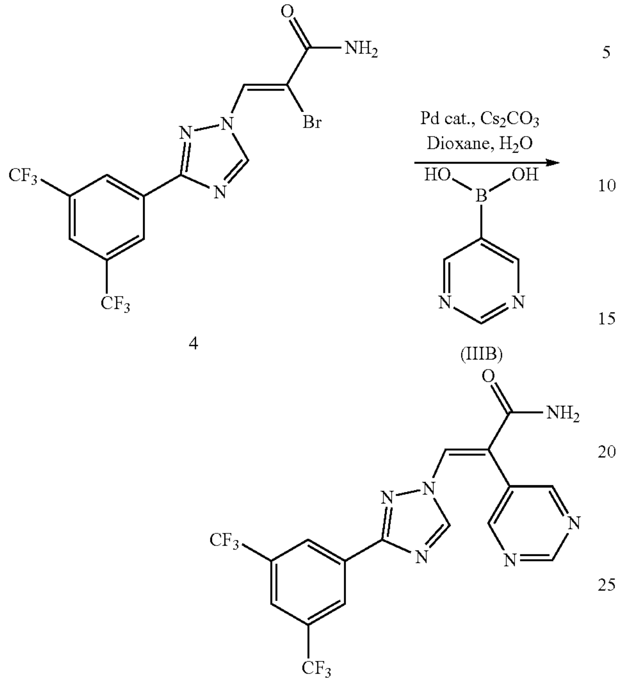

4

(IIIB)

KPT-8602 (MB6)

5

In this study, a scalable process for the manufacture of compound 5, (E)-3-(3-(3,5-bis(trifluoromethyl)phenyl)-1H-1,2,4-triazol-1-yl)-2-(pyrimidin-5-yl)acrylamide (MB6/KPT-8602) was developed.

The following HPLC protocol can be used.

Apparatus:

1. UPLC column: Agilent Zorbax SB-CN, 3.0×100 mm, 1.8 μm
2. Detector: 260 nm
3. Column temp: 60° C.
4. Mobile phase: A: 0.1% TFA in $H_2O$
   B: 50% ACN: 45% MeOH: 5% $H_2O$
5. Flow rate: 0.5 ml/min
6. Injection volume: 4 μL
7. Run time: 35 minutes
8. Gradient:

| Time (min) | % A | % B |
|---|---|---|
| 0.0 | 75 | 25 |
| 5.0 | 75 | 25 |
| 21.0 | 55 | 45 |
| 25.0 | 30 | 70 |
| 30.0 | 30 | 70 |
| 31.0 | 75 | 25 |
| 35.0 | 75 | 25 |

Figure 19:
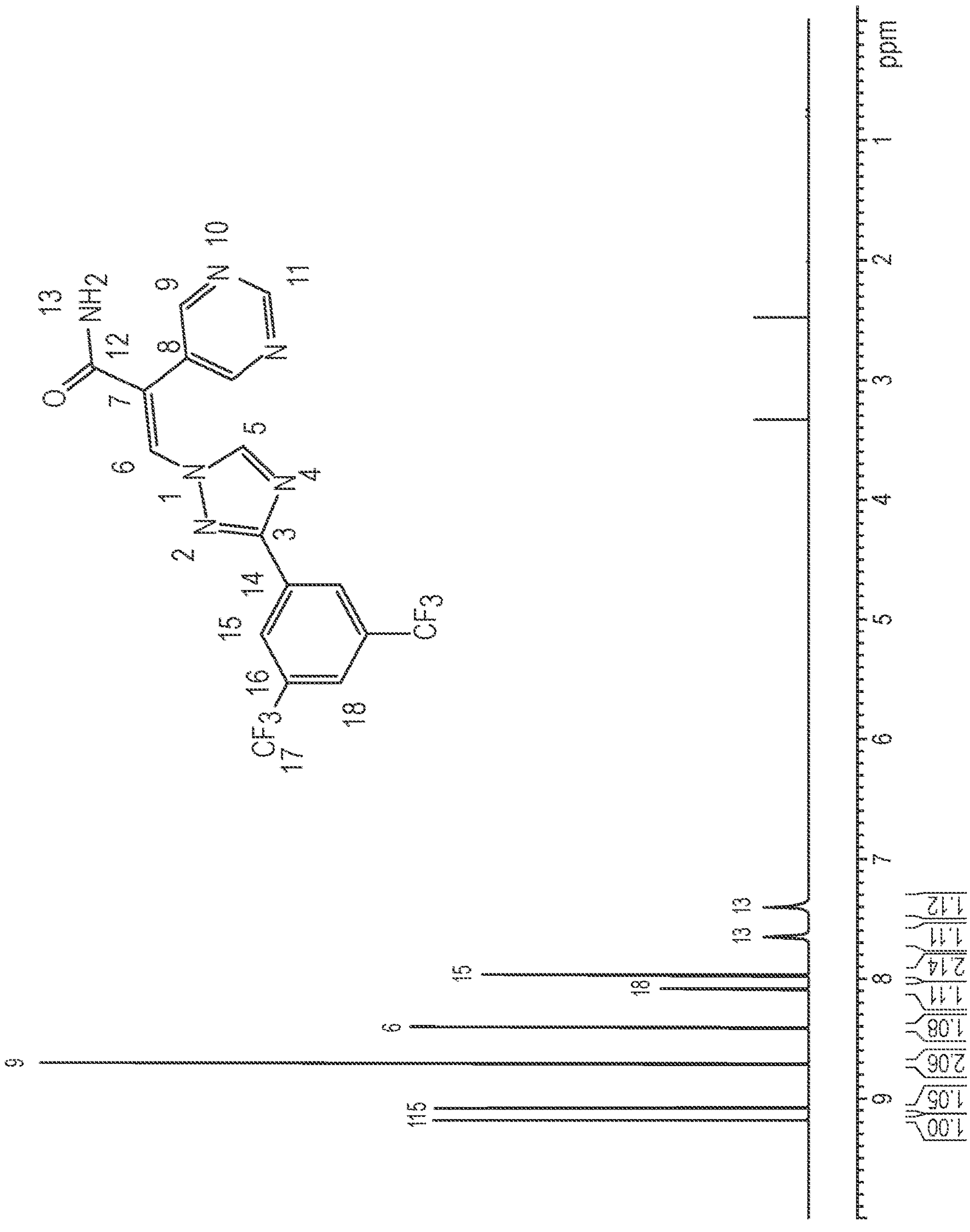
FIG. 19 shows a $^{1}H$ NMR of the compound MB6 (5) (see FIG. 1).

9. Dissolution Solvent (DS): (75% ACM: 25% $H_2O$)+0.1% TFA
10. Purge solvent: 50% ACN: 50% $H_2O$
11. Needle Wash: 50% ACN: 50% $H_2O$
12. Thermo Scientific 'Targer' all-plastic disposable Luer-Lok syringe, 3 ml or equivalent (must be compatible with ACN/$H_2O$ DS)
13. 0.2 μm PTFE filter
14. BECTON DICKINSON & CO. (B-D) prepackaged needle or equivalent Reagents and Standards 1. Acetonitrile (ACN), Methanol (MeOH), Water ($H_2O$), HPLC grade or equivalent
2. Trifluoroacetic Acid (TFA), reagent grade or equivalent
3. MB3 (KPT-9508) impurity standard: use current reference standard
4. MC8 (KPT-9506) impurity standard: use current reference standard
5. KG1 (KPT-454) impurity standard: use current reference standard
6. KF9 (KPT-452) impurity standard: use current reference standard
7. MC0 (KPT-8781) impurity standard: use current reference standard
8. MB6 (KPT-8602) reference standard: Use current reference standard A $^1$H NMR of the final product, compound KPT-8602/MB6/5, is shown in FIG. 19.

Having realized the poor selectivity of the utilized palladium tetrakistriphenylphosphine, a more robust and selective Pd catalyst (i.e. Strem amphos palladacycle gen. 2 (Cat #46-0342)) was found by screening several catalysts for the Suzuki coupling of this step. Based on the new catalyst system, the process was further evaluated by studying several key process parameters, i.e. the stoichiometry of Strem amphos palladacycle gen. 2 (Cat #46-0342) and boronic acid (compound represented by structural formula (IIIB), MB7), the reaction solvent and solvent ratio, the solvent volume, the reaction temperature, and different bases. Other issues, such as the MB7 degradation, simplifying the process operation, the conditions for the crude product isolation (MB6 methanol solvate, crystalline Form II described herein) and the MB6 recrystallization in MIBK to produce crystalline Form I as described herein and finally the Pd and MB7 residual levels of each in isolated product were also studied. It was found that the palladium removal from the crude product through treatment with Si-DMT silica scavenger is not required (but is permitted) in the improved process as the palladium level of the crude product was routinely below the current limit (NMT 400 ppm).

Surprisingly, the new reaction system was found to be very robust, performing well without vigorous degassing. The new process has been carried out at 15.5 g scale in demonstration experiments and successfully generated 81-86% overall yields of compound 5 (MB6 (KPT-8602) as represented by Structural Formula (VII)) as crystalline Form I. The yield of 81-86% is a significant improvement over the 26-49% reported yields of the previous process. Purity of the product was very good (HPLC purity was 100% a/a) with acceptable levels of Pd and boronic acid MB7.

GENERAL REACTION CONDITIONS STEP 3: Based on experiments assessing various process parameters for Step 3 (discussed in detail below) the following reaction conditions were used: about 1.0 eq. MB5, about 2.0 eq. MB7, about 0.5 eq. $Cs_2CO_3$, about 24 parts of degassed dioxane:$H_2O$ 7:1 v/v, 2 mol % Strem amphos palladacycle gen. 2 (Cat #46-0342), 7-7.5 hours at 55-60° C. All eq. are with respect to (wrt) MB5.

Isolation of Methanolate (Form II)—General Procedure 1:

A general isolation procedure for Form II (methanolate precursor to the final Form I) is as follows: After the 7-7.5 hour reaction time at 55-60° C. (see general reaction conditions above), the reaction mixture is adjusted to about 40-45° C. followed by charging of a slurry of celite (about 0.5 parts wrt MB5) and dioxane:water at about 7:1 v/v (about 2.5 parts wrt MB5). The resulting suspension is agitated at about 40-45° C. for about 15-20 min. The reaction mixture is filtered and the filter cake washed with dioxane:water about 7:1 v/v (at about 40-45° C., about 3 parts wrt MB5). The resulting filtrate is subjected to vacuum distillation and is distilled to a target volume of about 4.5-5.5 parts wrt MB5. The resulting suspension is adjusted to an internal temperature of about 50-55° C. The reaction mixture is then charged with MeOH (about 20 parts wrt MB5) portionwise. The suspension is then agitated at about 50-55° C. for about 60-70 min. The reaction mixture is then cooled to about 20-25° C. and then further cooled to about 0-5° C. over about 2-2.5 hours and is maintained at that temperature for a period of about 2-2.5 hours. The resulting suspension is then filtered and the filter cake washed with MeOH (about 10 parts wrt MB5). The cake is then dried.

Isolation of Form I— General Procedure 2:

The dried filter cake from General Procedure 1 is then transferred to a flask equipped with an overhead stirrer, thermometer and nitrogen inlet and Si DMT (about 5 eq. wrt MB5) is charged to the flask. MIBK is then charged to the flask (about 25 parts wrt MB5). The reaction mix is then heated to an internal temperature of about 65-70° C. and maintained at that temperature for about 1-1.5 hours if no scavenger used and about 4-5 hours if scavenger is used. The reaction mixture is then filtered hot at about 65-70° C. into a clean flask equipped with an overhead stirrer, thermometer and nitrogen inlet. The filter is washed with MIBK (at about 65-70° C., about 1.0 part wrt MB5). With agitation, the filtrate is slowly cooled to about 20-30° C. over about 3-3.5 hours, and then distilled under vacuum to a target volume of about 3-4 parts wrt MB5. The batch temperature is adjusted to about 55-60° C. and the reaction mixture is agitated at 55-60° C. for about 2-2.5 hours. Then the suspension is cooled to about 0-5° C. over about 2-2.5 hours and is stirred at this temperature for a minimum of about 1 hour. The reactions mixture is then filtered and the resulting cake is washed with MIBK (about 1.0 part wrt MB5 at about 0-5° C.).

The general procedures above were followed on a 15.5 g scale. Variations in the procedure (amounts used, temperatures, time, etc.) can occur while still obtaining a good yield and purity. Additional examples of isolation (General Procedure 1) and recrystallization conditions (General Procedure 2) are also provided below.

15.5 g Scale of General Procedures 1 and 2

A 500 mL four neck round bottom flask was equipped with an overhead stirrer, a thermometer, reflux condenser and $N_2$ bubbler. The flask was flushed with nitrogen for a minimum of 30 minutes. Under a $N_2$ flow, to the flask was charged with 15.5 g of compound 4 (MB5) (36.1 mmol, 1.0 eq.), 8.95 g of MB7 (72.2 mmol, 2.0 eq. wrt MB5), 5.88 g of $Cs_2CO_3$ (18.0 mmol, 0.5 eq. wrt MB5) and 0.415 g of Pd catalyst PT4 (Strem Amphos Palladacycle Gen. 2, cat. #46-0342, 0.72 mmol, 0.02 eq. wrt MB5), followed by charging 326 mL of degassed 1,4-dioxane (21 parts wrt MB5) and 47 mL of degassed water (3 parts wrt MB5).

With moderate agitation, the reaction mixture was then further degassed by bubbling nitrogen through it for a period of 60-70 minutes. The reaction mixture was then heated to an internal temperature of 55-60° C., and was maintained at that temperature for a period of 7-7.5 hours. The reaction temperature was adjusted to 40-45° C., and an IPC sample was taken. Upon completion, the reaction mixture was adjusted to 40-45° C., followed by charging a slurry of 7.75 g of celite (0.5 parts wrt MB5) and 39 mL of dioxane:water 7:1 v/v (2.5 parts wrt MB5). The resulting suspension was agitated at 40-45° C. for 15-20 minutes. The reaction mixture was filtered and the filter cake was washed with 46.5 mL of pre-warmed dioxane:water 7:1 v/v (40-45° C., 3 parts wrt MB5). The resulting filtrate was subjected to vacuum distillation and was distilled to a target volume of 70-85 mL (4.5-5.5 parts wrt MB5). The resulting thick suspension was adjusted to an internal temperature of 50-55° C. To the reaction mixture at 50-55° C. was then charged 310 mL of MeOH (20 parts wrt MB5) portionwise. The suspension was then agitated at 50-55° C. for a period of 60-70 minutes. The reaction mixture was then cooled to 20-25° C. and then further cooled to 0-5° C. over 2-2.5 hours and was maintained at that temperature for a period of 2-2.5 hours. The resulting suspension was then filtered through a Buchner funnel using a Whatmann filter paper and the filter cake was washed with 155 mL of MeOH (10 parts wrt MB5). The cake was then dried under vacuum at 45-50° C. for about 4.5 hours. Crystalline Form II (the methanolate) was obtained in 89% yield. Purity of the product was very good (HPLC purity was 99.3% to 99.4 area % with acceptable levels of Pd and boronic acid.

The dried filter cake was then transferred to a 500 mL three-necked round botton flask equipped with an overhead stirrer, a thermometer and a nitrogen inlet, followed by charging 0.25 g of SiDMT (5 eq. wrt MB5 (230 ppm of residual Pd). [The following calculation can be used to determine, based on residual palladium level, how much DMT silica to charge. To calculate mm Pd in the product: Mmol Pd=ppm Pd×g product/106.42×100 and Scavenger Charge=mmol Pd×4 eq./Scavenger loading (mmol/g).] To the solids was then charged 390 mL of 4-methyl-2-pentanone, also referred to herein as MIBK (25 parts wrt MB5). The reaction mixture was then heated to an internal temperature of 65-70° C. and maintained at that temperature for a period of 4-5 hours when scavenger treatment is conducted (if no scavenger treatment then 1-1.5 hours is sufficient). The reaction mixture was then filtered hot at 65-70° C. through a Buchner funnel (with a Whatmann filter paper) into a new 500 mL three-necked round bottom flask equipped with an overhead stirrer, a thermometer and a nitrogen inlet. The filter paper was then washed with 15 mL of pre-warmed MIBK (65-70° C., 1 part wrt MB5). With agitation the filtrate was slowly cooled to 20-30° C. over 3-3.5 hours, and then distilled under vacuum to a target volume of 50-55 mL (3-4 parts wrt MB5). The bath temperature was adjusted to 55-60° C. and the reaction mixture was agitated at 55-60° C. for 3-3.5 hours. The suspension was cooled to 0-5° C. over 2-2.5 hours and was stirred at the temperature for a minimum of 1.0 hour. The reaction mixture was then filtered through a Buchner funnel using a Whatmann filter paper. The cake was then washed with 15.5 mL of pre-cooled MIBK (1.0 part wrt MB5) at 0-5° C. The filter cake was then dried in a vacuum oven at 48-53° C. for 1-2 hours to provide the product (crystalline Form I) as a solid. The overall yield was 81-86%, HPLC purity was 100.0% a/a with acceptable level of Pd and boronic acid.

Isolation of Form I—General Procedure 2A:

Crude MB6 methanolate Form II is charged to a reactor followed by about 18 volumes of MIBK. The slurry is heated to about 80-85° C. to generate a solution. At this point, SiliaMetS® DMT (also referred to herein as SiDMT and being a silica-bound 2,4,6-trimercaptotriazine (trithiocyanuric, TMT) scavenger in about 1 volume of MIBK can be charged to the reactor for the removal of Pd. The use of this scavenger is optional. The solution (no scavenger) or slurry (with scavenger) is then mixed for a period of time. Once that time is complete, the solution/slurry is polish filtered hot to a clean reactor while maintaining a temperature of about 80-85° C. 2 volumes of MIBK is then charged to the original reactor and heated to about 80-85° C. Once at temperature the solvent is transferred to the batch via the polish filtration apparatus as a rinse of the reactor/filtration system. The solution is then cooled slightly to induce nucleation during a hold period. Following confirmed nucleation, the solids are crystallized via a controlled cooling crystallization with a final temperature of 0-5° C. The slurry is held at this temperature for an appropriate time to complete crystallization and then the solids are isolated via filtration. About 2 volumes of MIBK are polish filtered to the reactor and cooled to about 0-5° C. Once at temperature the wash is charged to the cake in two portions and pulled through the cake with suction. Following completion of the wash, the solids are dried and packaged.

17 g Scale of General Procedure 2A:

17 g of crude MB6 (methanol solvate Form II) was weighed into a 400 ml Easy max vessel. About 306 mL of 4-methyl-2-pentanone (MIBK; 18 V wrt MB6 methanolate) was added. The mixture was stirred moderately and warmed to about 80-85° C. to dissolve the solid. About 0.51 g of Si DMT (3%. wrt MB6 (methanolate Form II) was charged to the vessel. About 18 mL of MIBK (2V×0.51 g+1V rinse) was charged to the vessel. The mixture was stirred moderately for about 4.5 h at about 80-85° C. The reaction mixture was then filtered hot at about 80-85° C. through a Buchner funnel (with a Whatmann filter paper) into a 500 mL erlenmeyer flask. The filter paper/SiDMT/$Cs_2CO_3$ was then washed with about 34 mL of pre-warmed 4-methyl-2-pentanone/MIBK (about 80-85° C.; about 2 V wrt MB6 as the methanolate Form II). The easy max vessel was cleaned and the contents of the Erlenmeyer containing the filtrate and wash was warmed to about 80-85° C. and put back in the easy max vessel. The batch temperature was adjusted to about 80-85° C. and the reaction mixture was agitated for about 30 min to reach dissolution. Then the solution was cooled to about 20-25° C. over a minimum of 3 hours. Then the suspension was cooled to about 0-5° C. over about 2-2.5 hours and was stirred at this temperature for a minimum of about 1.0 hour. The reaction mixture was then filtered through a Buchner funnel using a Whatmann filter paper.

The cake was then washed with about 34 mL of pre-cooled 4-methyl-2-pentanone/MIBK (about 2 vol wrt MB6 methanolate Form II; at about 0-5° C.). The filter cake was then dried in a vacuum oven at about 25-30° C. for about 3 hours to provide the product as a white solid (% Yield 75%, Purity=99.98% a/a).

Pd-Catalyzed Suzuki Coupling Reaction Assessment of Catalyst

The results of the initial Pd catalyst assessment are summarized in the table presented in FIG. 2. A baseline experiment was carried out using Pd(dppf)$Cl_2$·DCM, (FIG. 2; Entry 1). As previously observed, the baseline experiment showed incomplete conversion (71.1% a/a) and significant levels of debromination (15.8% a/a).

Screening with a series of crotyl based pre-catalyst systems showed improved results especially when bulky electron rich ligands were used such as Amphos and $P(tBu)_3$ (FIG. 2; Entries 3 and 4). $P(tBu)_3$ was found to perform slightly better than Amphos, giving a: higher level of conversion (93.5 vs. 81.3% after 24 hours). The $P(tBu)_3$ was repeated and found to give similar performance (97.2% a/a conversion) showing reproducibility (FIG. 2; Entry 11). Of note also is that the debromination pathway was significantly lowered (3.8-5.7% a/a). Interestingly, a previously uncharacterized impurity with m/z=699 (ESI) was identified in the screening study. The tentative structure (PF9) was assigned based on the observed mass. This impurity is hypothesized to arise from a side reaction involving Heck-type coupling between MC8 and MB5. On the basis of the results described above, $tBu_3PPd$(crotyl)Cl was identified as a desirable catalyst for the further process development.

The three impurities shown below were the major by-products of this Suzuki coupling and their levels after reaction was a key factor in evaluation of the performance of the coupling.

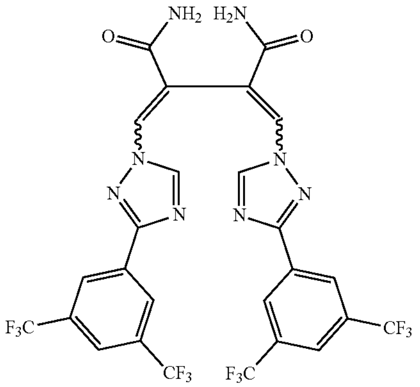

Exact Mass: 698.10

PF9

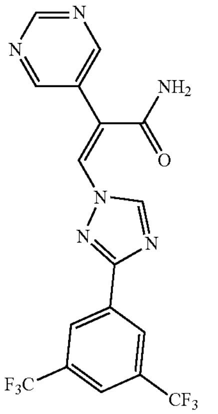

MC0, isomer of MB6

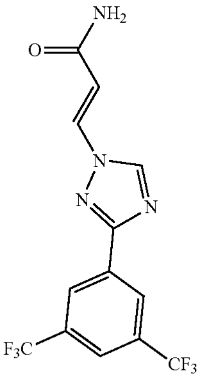

MC8

The reaction solvents were also screened for the Pd catalytic reaction. These results are summarized in FIG. 3.

The reactions running in dioxane/$H_2O$, THF/H20, and EtOH/MeTHF/$H_2O$ gave a 100% conversion with good product purity. However, there were still significant amounts of impurity formation. The reactions in both MeTHF/$H_2O$ and toluene/MeTHF/$H_2O$ were observed to stall. Therefore, the THF/$H_2O$ solvent system showed potential for further evaluation. The Suzuki coupling was tried using different kinds of bases. FIG. 4 below summarized the results. $Cs_2CO_3$ was found to give the best performance among these 4 bases.

Further Process Investigations

For this work, a single lot of MB5 with high HPLC purity (99.5% a/a) was used, except where noted.

Initially, the catalyst system $tBu_3PPd$(crotyl)Cl) identified as a desirable catalyst above was run in a 4.3 g scale reaction. The reaction conditions were chosen as 1.0 eq. MB5, 2.0 eq. of boronic acid MB7, 0.5 eq. cesium carbonate, and 3% $tBu_3PPd$(crotyl)Cl in 16 parts of degassed $THF/H_2O$ 15:2 v/v at reflux (63° C.) (The reaction mixture as a suspension was degassed for 20-30 minutes before heating). After 4 hours at reflux, the IPC showed that the residual MB5 wrt MB6 was 115% a/a (the reaction had stalled after one hour), while a significant amount of MC8 (21% a/a wrt MB6) was generated. The coupling could be re-activated after charging additional Pd catalyst (2 mol % more). However, the reaction was observed to stall again at 55% a/a of residual MB5 wrt MB6. This reaction was re-run under similar conditions and the results are summarized in FIG. 5.

These results showed that these reaction conditions did not give reproducible results. Additional catalyst were assessed and the results are summarized in FIG. 6.

It was found that both JM Amphos Pd(crotyl)Cl (Pd-161) and Strem Amphos Palladacycle Gen. 2 (Cat #46-0342) provided the same excellent results when dioxane: $H_2O$ was used as the solvent system for the reaction (FIG. 6; Entries 5, 6 and 7), with much lower levels of impurities. When the Strem Amphos palladacycle gen. 2 was used with THE: $H_2O$ as the solvent system (Table 6; Entries 3 and 4) there was an increase in the impurities that were generated. Both JM Amphos Pd(crotyl)Cl (Pd-161) and Strem Amphos palladacycle gen. 2 (Cat #46-0342) as the Suzuki coupling catalysts showed better selectivity and robustness than the $tBu_3PPd$(crotyl)Cl.

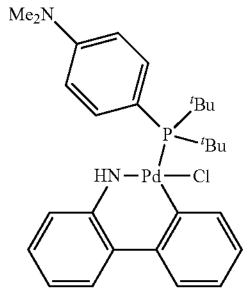

Strem Amphos Palladacycle Gen. 2 (Cat #46-0432)
PT4

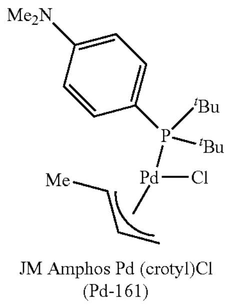

JM Amphos Pd (crotyl)Cl
(Pd-161)

The Strem Amphos palladacycle gen. 2 (Cat #46-0342) and JM Amphos catalyst are suitable as the active catalytic system.

FIG. 7 summarizes the results of experiments that were carried out to examine the effect of catalyst stoichiometry on the performance of the chemistry. These results demonstrate that there is a comparable performance between 2 mol % and 3 mol % Pd catalyst, while reaction stalling was observed when catalyst was reduced below 2 mol %. It may be possible to further reduce the catalyst loading.

The amount of the boronic acid MB7 should be minimized to avoid undesirable effects. Experiments were carried out to explore the lower boundary for MB7 equivalents. FIG. 8 summarizes these studies.

The reaction was observed to stall when the boronic acid was reduced to 1.5 eq., even when 3 mol % Pd catalyst was used. The residual MB5 after reaction completion was very close to the limit (<1% a/a) when the boronic acid was 1.8 eq. In order to ensure that the Suzuki coupling was robust, a slightly higher level (2.0 eq.) of MB7 was set in the finalized procedure for this process. Of note is that the excess remaining MB7 was successfully purged during the product isolation steps.

Several solvent systems were examined to optimize the Suzuki coupling. The experimental results are listed in FIG. 9.

Dioxane:water was identified as a beneficial system since a cleaner reaction was obtained, while the other solvent systems resulted in either stalling or higher levels of impurities. Although dioxane is a class 2 solvent and has a lower ICH limit than other solvents, the dioxane:water solvent system was still chosen for the final process since dioxane gave superior performance and could be reduced to meet the required limit in the final API after product isolation/recrystallization operations, which was demonstrated in the previous GMP production.

The ratios of dioxane:water solvent system were further evaluated, and the results are summarized in FIG. 10. A reduction in water (14:1 v/v dioxane:water; FIG. 10, Entry 1) slowed the reaction down, while higher water (2:1 v/v dioxane:water; FIG. 10, Entry 3) resulted in a higher level of impurities. 7:1 v/v dioxane:water gave the best result and therefore was set as the final solvent ratio for this process.

Total solvent volume for this coupling was also evaluated. FIG. 11 is the summary of these experimental results.

There was a comparable performance between 24 parts and 34 parts (FIG. 11; Entries 1 and 2). While 18 pts was also deemed acceptable, the performance declined. The coupling stalled when 12 parts were employed (possibly due to the resulting biphasic reaction conditions). Therefore, the volume for this coupling was chosen to be 24 parts for the final process.

Reaction temperature for this Suzuki coupling was also examined. The summarized results of this study are tabulated in FIG. 12.

Elevated temperature (71-72° C.; Entry 4 in FIG. 12) gave an increased level of MC0 (Z isomer) Reaction at 50-55° C. (Entry 1 in FIG. 12) was slightly cleaner but slower. Reaction at 55-60° C. or 60-65° C. resulted in a comparable performance. The final process was set at 55-60° C.

FIG. 13 is a comparison of results from degassed and non-degassed reactions (after reagents/solvent combination) for the Suzuki coupling.

The Suzuki coupling was found to perform well without vigorous degassing after reagent/solvent combination. Degassing the reaction mixture before heating can be implemented if desired to ensure robustness.

Several bases were evaluated alongside a boronic acid degradation study which will be discussed later. These different base studies also can be considered to evaluate pH as a factor that could affect the performance of the reaction. The related results are summarized in FIG. 14.

When using $K_3PO_4$ to replace $Cs_2CO_3$ (FIG. 14, Entry 2), the reaction stalled. When a 1:1 mix of 0.25 eq. $Cs_2CO_3$/0.25 eq. $CsHCO_3$ (FIG. 14, Entry 3) was used, the reaction also stalled, but it could be reinitiated by charging more $CsHCO_3$ (0.25 equiv), thereby increasing the base charge to a level equal to that of the reference conditions (FIG. 14, Entry 1). A reaction using a mix of 0.25 eq $Cs_2CO_3$/0.50 eq CsOH (FIG. 14, Entry 4) showed a comparable performance with using $Cs_2CO_3$ only. These results indicate that variations in $CO_2$ off-gas rate are unlikely to impact process performance on scale-up.

As noted about under GENERAL REACTION CONDITIONS STEP 3, upon completion of the above set of experiments, the following reaction conditions were recommended: 1.0 eq. MB5, 2.0 eq. MB7, 0.5 eq. $Cs_2CO_3$, 24 parts of degassed dioxane:$H_2O$ 7:1 v/v, 2 mol % Strem amphos palladacycle gen. 2, 7-7.5 hours at 55-60° C. Notable changes and improvements relative to the prior procedures are summarized in FIG. 15A and FIG. 15B.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A crystalline form of the compound represented by the following Structural Formula (VII):

(VII)

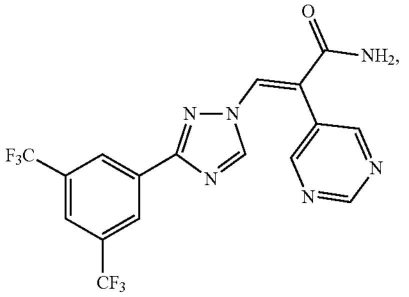

wherein the crystalline form is characterized by x-ray powder diffraction peaks at 2θ angles of 4.6°, 22.8°, 23.2°, and 24.4°.

2. The crystalline form of claim 1, wherein the crystalline form is characterized by x-ray powder diffraction peaks at 2θ angles of 4.6°, 20.0°, 22.8°, 23.2°, and 24.4°.

3. The crystalline form of claim 1, wherein the crystalline form is characterized by x-ray powder diffraction peaks at 2θ angles of 4.6°, 19.0°, 20.0°, 22.8°, 23.2°, 23.7°, 24.4°, and 27.9°.

4. The crystalline form of claim 1, wherein the crystalline form is characterized by an x-ray powder diffraction pattern substantially in accordance with that depicted in FIG. 20.

5. The crystalline form of claim 1, wherein the crystalline form is characterized by a DSC thermogram having an endothermic event at about 226° C.

6. The crystalline form of claim 1, wherein the crystalline form is characterized by a DSC thermogram substantially in accordance with that depicted in FIG.

7. A method of preparing a compound represented by structural formula (VII), (VII)

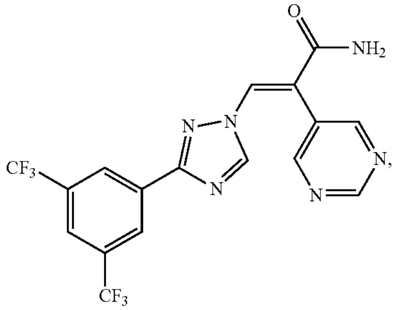

comprising:

reacting a compound represented by structural formula (II), (II)

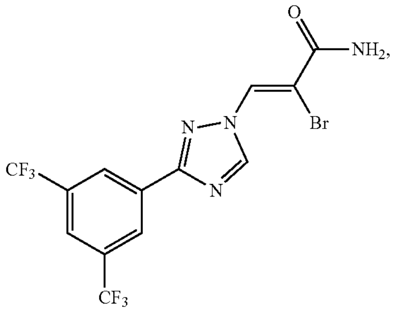

with a compound represented by structural formula (III), (III)

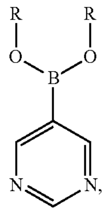

in a first solvent, in the presence of a Pd catalyst and one or more inorganic bases under conditions suitable to prepare a compound represented by structural formula (VII), wherein:

each R is hydrogen, a $C_1$-$C_4$ alkyl, or two groups R, taken together with the oxygen atoms to which they are attached, form a 5-7 member cyclic acetal moiety, and thereby obtaining the compound represented by structural formula (VII), wherein the Pd catalyst is selected from chloro {[4-(N,N-dimethylamino)phenyl]di-t-butylphosphino}(2'-amino-1,1'-biphenyl-2-yl)palladium(II) or chloro(crotyl) [di-tert-butyl (4-dimethylaminophenyl)phosphine]palladium (II).

8. The method of claim 7, wherein the one or more inorganic base is selected from a quaternary ammonium, sodium, potassium, or cesium carbonate, bicarbonate, acetate, or hydroxide.

9. The method of claim 7, wherein the compound represented by structural formula (III) is a compound represented by structural formula (IIIB):

(IIIB)

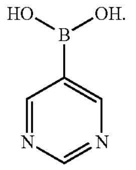

10. The method of claim 7, wherein the inorganic base is $Cs_2CO_3$ or CsOH.

11. The method of claim 7, wherein the Pd catalyst is chloro {[4-(N,N-dimethylamino)phenyl]di-t-butylphosphino}(2'-amino-1,1'-biphenyl-2-yl)palladium(II).

12. The method of claim 7, wherein a Pd catalyst load is from 0.5% to mol % to 10 mol %.

13. The method of claim 7, wherein an amount of the inorganic base is from 0.5 to 2 molar equivalents of base with respect to the compound represented by structural formula (II).

14. The method of claim 7, wherein the conditions suitable to prepare the compound represented by structural formula (VII) comprise:

a Pd catalyst load from 0.5 mol % to 3 mol %;

an amount of the compound represented by structural formula (III) of from 1.0 to 2.2 molar equivalents with respect to the compound represented by structural formula (II);

an amount of the inorganic base of 0.8-1.2 total molar equivalents of base with respect to the compound represented by structural formula (II);

the first solvent comprises from 16 parts to 21 parts of dioxane and from 2 parts to 3 parts of water;

a reaction temperature from about 55° C. to about 60° C.; and a reaction time of about 7-8 hours.

15. The method of claim 7, further comprising a step of preparing the compound represented by structural formula (II), (II)

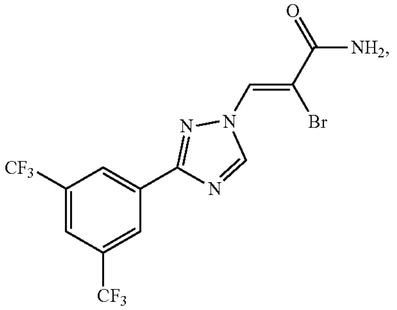

by dehydrobrominating a compound represented by structural formula (IV), (IV)

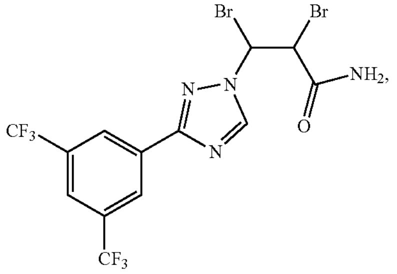

in a second solvent, in the presence of an organic base, under conditions suitable for producing the compound represented by structural formula (II).

16. The method of claim 15, further comprising a step of preparing the compound represented by structural formula (IV), (IV)

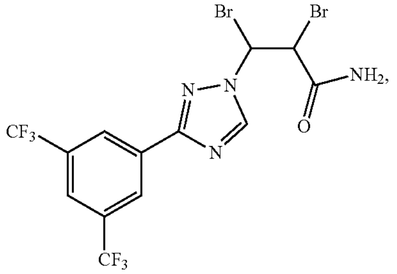

by reacting a compound represented by structural formula (V), (V)

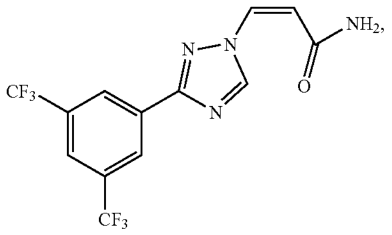

with bromine ($Br_2$) in a third solvent, in the presence of a bromide salt, under conditions suitable to prepare the compound represented by structural formula (IV).

17. The method of claim 15, wherein the second solvent comprises about 11 parts of ACN and about 4 parts of $H_2O$ with respect to the compound represented by structural formula (IV), the organic base is DIPEA, and wherein the conditions suitable for preparing the compound represented by structural formula (II) comprise:

an amount of DIPEA of about 1 molar equivalent with respect to the compound represented by structural formula (IV);

a reaction temperature of from 20° C. to 25° C.; and a reaction time from 2 to 3 hours.

18. The method of claim 16, wherein the third solvent comprises acetic acid.

19. The method of claim 16, further comprising a step of preparing a compound represented by structural formula (V), (V)

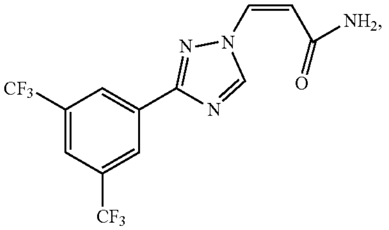

by amidating a compound represented by structural formula (VI), (VI)

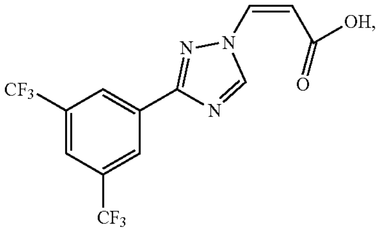

in a fourth solvent, with an amidating agent, in the presence of a tertiary amine organic base and a chloroformate, under conditions suitable for producing the compound represented by structural formula (V).

20. A compound represented by structural formula (V)

(V)

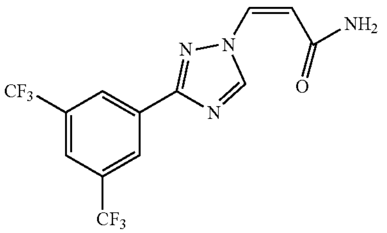

or a salt thereof.

21. A method of preparing crystalline form of the compound represented by Structural Formula (VII), wherein the crystalline form is characterized by x-ray powder diffraction peaks at 2θ angles of 4.6°, 22.8°, 23.2°, and 24.4°

(VII)

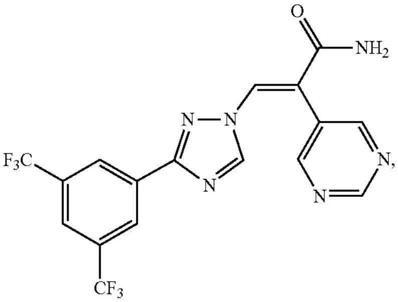

the method comprising:

(a) contacting crystalline form of the compound represented by Structural Formula (VII) characterized by x-ray diffraction peaks at 2θ angles 9.9°, 19.2°, 22.4°, and 24.4° with about 18 volumes of 4-methyl-2-pentanone (MIBK) to form a mixture;

(b) heating the mixture of step (a) to about 80-85° C. to form a heated mixture;

(c) optionally adding to the heated mixture of step (b) SiDMT;

(d) maintaining the heated mixture at a temperature of about 80-85° C. for about 4.5 hours;

(e) filtering the heated mixture to obtain a filtrate;

(f) adding MIBK at a temperature of about 80-85° C. to the filtrate;

(g) inducing nucleation of the crystalline form of the compound represented by Structural Formula (VII), wherein the crystalline form is characterized by x-ray power diffraction peaks at 2θ angles of 4.6°, 22.8°, 24.4° in the filtrate by cooling the filtrate to about 20-25° C.;

(h) crystallizing the crystalline form of the compound represented by Structural Formula (VII), wherein the crystalline form is characterized by x-ray powder diffraction peaks at 2θ angles of 4.6°, 22.8°, 23.2°, and 24.4° by a controlled cooling crystallization of the filtrate with a final temperature of 0-5° C.; and (i) isolating the crystalline form of the compound represented by Structural Formula (VII), wherein the crystalline form is characterized by x-ray powder diffraction peaks at 2θ angles of 4.6°, 22.8°, 23.2°, and 24.4° from the filtrate.

* * * * *